US012121457B2

(12) United States Patent
Hughes

(10) Patent No.: US 12,121,457 B2
(45) Date of Patent: Oct. 22, 2024

(54) MINIMALLY INVASIVE USE OF ROBOTIC APPENDAGE FOR SURGERY AND EXPANSIVE DEVICE AND SURGICAL IMPLANT

(71) Applicant: Douglas George Hughes, West Salem, WI (US)

(72) Inventor: Douglas George Hughes, West Salem, WI (US)

( * ) Notice: Subject to any disclaimer, the term of this patent is extended or adjusted under 35 U.S.C. 154(b) by 149 days.

(21) Appl. No.: 17/592,013

(22) Filed: Feb. 3, 2022

(65) Prior Publication Data

US 2022/0175550 A1 Jun. 9, 2022

Related U.S. Application Data

(63) Continuation of application No. 16/380,355, filed on Apr. 10, 2019, now Pat. No. 11,266,511.

(60) Provisional application No. 62/656,127, filed on Apr. 11, 2018.

(51) Int. Cl.
| | |
|---|---|
| *A61F 2/46* | (2006.01) |
| *A61B 17/16* | (2006.01) |
| *A61B 34/20* | (2016.01) |
| *A61B 90/00* | (2016.01) |
| *A61F 2/44* | (2006.01) |
| *A61B 17/17* | (2006.01) |
| *A61B 17/70* | (2006.01) |
| *A61B 34/10* | (2016.01) |
| *A61B 34/30* | (2016.01) |

(52) U.S. Cl.
CPC ........ *A61F 2/4611* (2013.01); *A61B 17/1615* (2013.01); *A61B 34/20* (2016.02); *A61B 90/03* (2016.02); *A61F 2/442* (2013.01); *A61B 17/1671* (2013.01); *A61B 17/1757* (2013.01); *A61B 17/7032* (2013.01); *A61B 34/10* (2016.02); *A61B 34/30* (2016.02); *A61B 2090/031* (2016.02); *A61F 2/4455* (2013.01)

(58) Field of Classification Search
CPC ..... A61B 17/1615; A61B 90/03; A61B 34/20; A61F 2/4611; A61F 2/442
See application file for complete search history.

(56) References Cited

U.S. PATENT DOCUMENTS

| | | | |
|---|---|---|---|
| 9,913,725 | B2 | 3/2018 | Roche et al. |
| 2009/0188965 | A1 | 7/2009 | Levin et al. |
| 2010/0057087 | A1 | 3/2010 | Cha |
| 2011/0152867 | A1 | 6/2011 | Petrzelka et al. |
| 2011/0295370 | A1 | 12/2011 | Suh et al. |
| 2015/0320570 | A1 | 11/2015 | Suh et al. |
| 2016/0174970 | A1 | 6/2016 | Shelton, IV et al. |
| 2017/0265774 | A1* | 9/2017 | Johnson ................. A61B 34/32 |

FOREIGN PATENT DOCUMENTS

| | | |
|---|---|---|
| WO | 2008/031245 A2 | 3/2008 |
| WO | 2013/028365 A1 | 2/2013 |

* cited by examiner

*Primary Examiner* — Sameh R Boles
(74) *Attorney, Agent, or Firm* — Amanda M. Prose; Westman, Champlin & Koehler, P.A.

(57) ABSTRACT

A device for safely approaching vertebral disc space utilizing stereotactic guidance, clearing material from the disc space, a device for expanding the disc space, stereotactic methods for implant planning and monitoring articulating instrument end effectors and a device for implantation into the disc space for the purpose of fusion or disc replacement.

13 Claims, 21 Drawing Sheets

Articulating drill extension in use through DEAC

Fusion implant filling with graft cannula in place

MINIMALLY INVASIVE USE OF ROBOTIC APPENDAGE FOR SURGERY AND EXPANSIVE DEVICE AND SURGICAL IMPLANT

CROSS REFERENCE TO RELATED APPLICATION

The present application is a Continuation of U.S. patent application Ser. No. 16/380,355, filed Apr. 10, 2019, which is based on and claims the benefit of U.S. provisional patent application Ser. No. 62/656,127, filed Apr. 11, 2018, the content of which is hereby incorporated by reference in its entirety.

BACKGROUND

Back pain is one of the most common diagnoses in medicine today. As the population ages, back pain and other joint related issues create a large burden on our healthcare system. Spinal procedures to address back pain are increasing in both frequency and cost. Surgical interventions aimed at treating back pain have to deal with dysfunctional joints in the spine.

There are two overriding principles when treating degenerative joint disease surgically; replacement or fusion. Spinal fusions have long been the gold standard for treating pain caused by degenerative joint disease in the spine. Disc replacement surgery is a more recent surgical procedure designed to treat back pain while maintaining normal spinal motion. Both procedures are invasive, complicated, and costly.

Recent surgical trends are aimed at minimizing invasion and complications while also reducing procedure cost. Percutaneous pedicle screw placement has become a popular replacement for open pedicle screw placement. Tubular dilators or endoscopic systems are replacing open spine access techniques, providing smaller incisions with less tissue damage.

Intervertebral disc degenerative disease is implicated as a primary cause of back pain. Degenerative joint disease can also lead to neurologic deficits by causing stenosis of spinal spaces designated for neurologic tissue passage. Surgical approaches are designed to decompress and fuse or replicate the motion of the intervertebral disc space. These procedures require openings in the spine identical to or larger than the size of the stabilization device to be implanted. The disk space is made of an annular ring that circumferentially bounds the intervertebral space and contains the intervertebral cushion known as the nucleus pulposus. Surgical openings in the annulus are sized according to the implant that is used to stabilize the intervertebral space. An anterior approach for an interbody fusion is the gold standard because it allows the largest implantable stabilization device and the greatest quantity of fusion graft material to be placed. Fusion graft augmenters such as Infuse® by Medtronic are often utilized with anterior approaches because it can safely be kept away from neurologic structures. The annular opening however is similarly large. This creates instability that must be addressed by the surgical construct.

As an example, in anterior lumbar interbody fusions, the annular opening causes unstable extension of the spine. This must be addressed with instrumentation designed to limit that specific motion. Intervertebral disc replacements also require a large annular opening to be placed. They require endplate replication with metal plates anchored into the bony endplates above and below the disk space as a means of holding the device in the disc space. This causes considerable difficulty if the devices ever need to be removed. It also causes weakness in the bone that can cause endplate fractures if these devices are applied to adjacent segments.

Robotics is an evolving surgical field that aims to significantly minimize the exposure necessary to perform traditional tasks. The application of robotics to spinal surgery has thus far been limited to placement of spinal hardware. Intervertebral disc preparation is trivial through a large enough annular exposure, however, when the annular exposure is small, complete removal of the nucleus pulposus inside of the annulus is nearly impossible with today's tools. For example, the standard posterior discectomy approach makes it nearly impossible to remove the nucleus pulposus from the opposite side of the disk space particularly in the posterior region.

SUMMARY

An aspect of the present disclosure relates to an articulating drill extender and a method for articulating solid torque shafts using bevel gears. This articulating drill extender may be incorporated into standard handheld surgical equipment and additionally or alternatively may be controlled robotically.

The articulating drill extender utilizes a drill bit to mortselize the disc, remove endplate cartilage and prepare a bleeding bony surface if a fusion is the goal of surgery. The drill shaft can be connected to existing drill power sources or to a new drill device controlled by, for example, a surgeon or a surgical robot. The articulating drill extension may be a solid shaft terminating with one or more articulating gears present at the articulation joints of the drill. At each articulation, a new solid drill shaft interfaces with the previous to allow transmission of torque any at articulation angle between 0 and 90 degrees. The articulating torque delivery of the device can find application to other areas outside of medicine as well given its small size, proximal control of distal action and unparalleled ability to deliver high torque remotely to a constrained space.

Another aspect of the present disclosure relates to a hydrostatic disc space expansion device for insertion into a disc space within a patient in a first, compact state and configured to take its predetermined shape within the disc space to separate the discs or otherwise provide a space therein within the patient as the device is configured to take its predetermined shape after placement within the disc space.

Yet another aspect of the present disclosure relates to a formed interbody fixation device for rigid or motion-preserving stabilization within a patient. The fixation device has a predetermined shape selected and tailored for a specific patient's anatomy and assumes its predetermined shape when it is filled with the surgeon's choice the materials.

Another aspect of the present disclosure relates to a stereotactic drill extension access channel.

Another aspect of the present disclosure relates to a stereotactic solution for monitoring movable portions of stereotactic instruments.

Yet another aspect of the present disclosure relates to a planning solution for manufacture of purpose-built spinal implants.

Another aspect of the present disclosure relates to a surgery that is planned ahead of time utilizing additions to spinal planning software. The plan comprises the volume of disc to be resected and plan for sizing a spinal distractor and implant that will meet the patient's needs. The robot or robot-human combination then carries out the surgical plan.

Additionally, or alternatively the plan can be made in real time if the disc space requires mobilization prior to access. The robot utilizes stereotactic navigation to monitor patient anatomy location in the operative space. For example, a combination stereotactic frame/disc space access port may be placed under direct visualization or percutaneously using neurologic monitoring via electromyography and/or endoscopy. The access portal is rigidly fixed inside the patient's disk space or additionally can be held by the robot itself as a reference. It is through this port that the robot arm can complete the morselization of the disc's contents. Once the disk space preparation is complete the space is irrigated through the access portal and the fragments of discs are removed via suction. The annular ligament itself becomes a stabilizing structure in the fusion or disc replacement construct.

Another aspect of the present disclosure relates to a clip for securing a drill extension access channel to retractor system.

Yet another aspect of the present disclosure relates to a robotic arm extension for limiting motion of any instrument to be operated through the working channel of the instrument. Such an extension may be an adapter for an existing robotic arm extension with manual controls to be operated by the surgeon, or a purpose-built robotic arm extension where the robot is able to control the articulating drill extender limiters.

A robot can utilize a very small annular opening for disc space access thereby limiting any destabilization of a disc space. The disc removal is performed with a robotic appendage such as the articulating drill extension and which utilizes a hollow articulating arm with a drill shaft running through the central portion. The drill shaft may be held in a fixed trajectory by the robotic arm and operated by a human operator, or the drill arm can be completely controlled by the surgical robot. This device has applications in various surgical areas. Orthopedic operations, such as knee or hip replacements, are examples of procedures where these devices may be useful.

Another aspect of the present disclosure relates to a system for minimally invasive robotic access to an intervertebral space with placement of a collapsible device designed specifically to meet a patient's a surgeon's needs at the operative level, including spinal fusions and disc replacements. The method is designed to be used as a minimally invasive approach and leverage new robotic surgical technology.

DETAILED DESCRIPTION

Figure 1:
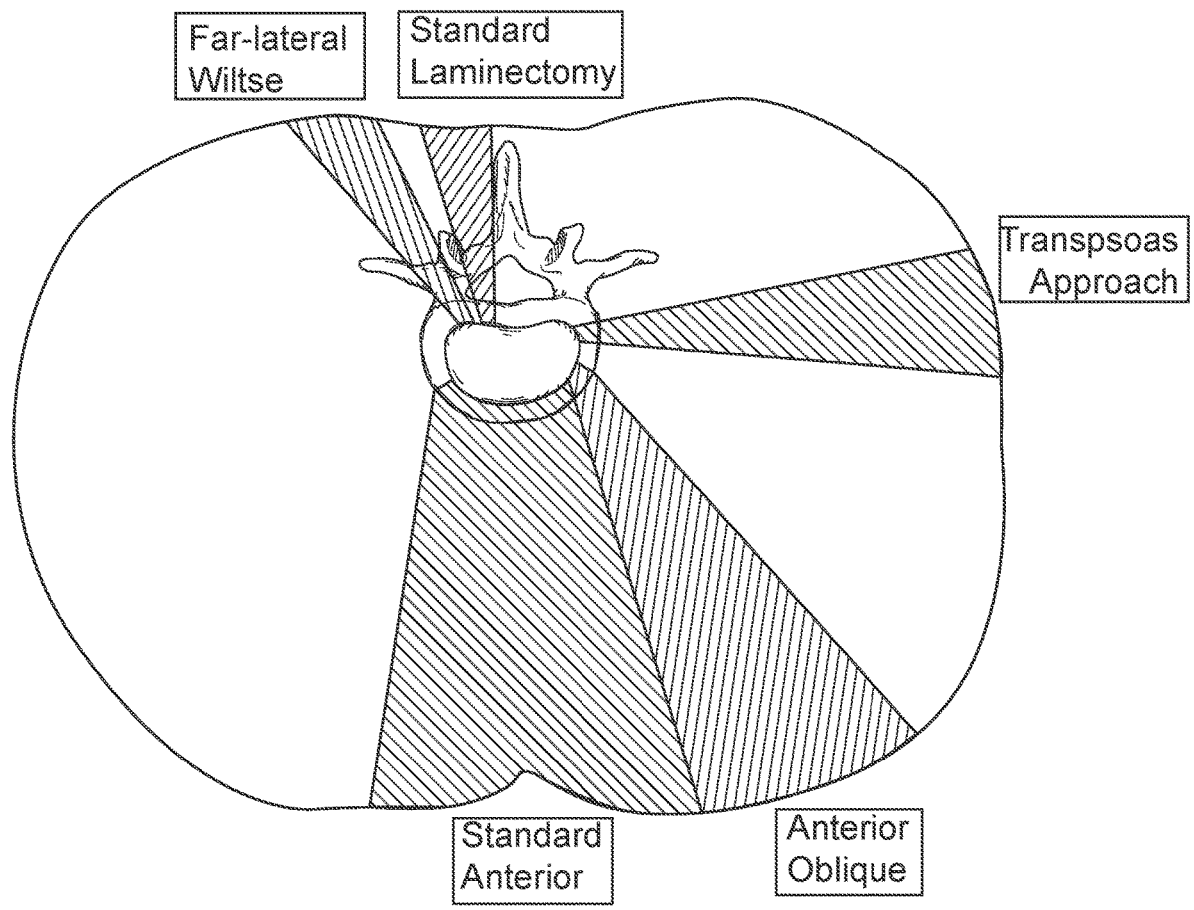
FIG. 1 illustrates standard spine access approaches used by spine surgeons.

A device for safely approaching the intervertebral disc space utilizing stereotactic guidance, clearing material from the disc space, a device for expanding the disc space, stereotactic methods for implant planning and monitoring articulating instrument end effectors and a device for implantation into the disc space for the purpose of fusion or disc replacement are described herein.

The device for safe approach to the disc space is a tube with an attached stereotactic fiducial tree. This tube is inserted into the disc space with a central dilator that allows the device to be placed into the disc space safely. The stereotactic tree allows current stereotactic systems to monitor the access tube's position. The tube itself allows work inside the disc space to occur while keeping neurologic structures safe.

The device for clearing the disc material may serve a wide variety of functions as this device is specifically designed to deliver high torque in small spaces with robotic control or assistance. It is an instrument that combines solid drill shafts with articulating gears. The drill shaft can operate any number of torque devices including standard drill bits and burrs, cutting channel suction ends or torque driven gripping or cutting end effectors. Novel stereotaxis techniques will allow for tracking of the device articulations virtually.

Additionally, planning software can be utilized prior to surgery for selection of proper expansion and implant devices. These devices can be standard, premade sizes or custom dimensioned devices manufactured on-demand. The disc expansion device described herein is a preformed shape that is pressurized with aqueous solution to hydrostatically lift the vertebral body endplates apart.

After the disc space is cleared and expanded, the implantable interbody device, also made into a predetermined shape, is placed into the disc space in a collapsed form and reconstituted with the desired fill material. This device can be formed as a container ring with an open center. This opening would be designed for application of fusion graft. The device could also be a multi-chambered device that could be filled with the desire disc replacement material. The device is specifically designed as a container for either rigid fill material such as cement or semi-rigid materials such as silicates or polyurethane. It has a central working channel built into it. This working channel is accessed using a fill tube. This device can be placed using any existing surgical approach to the spine. Its most useful application is through a standard lumbar discectomy approach. Other approaches such as far lateral, transpsoas, anterior oblique, and direct anterior are all possibilities as well. This device is designed specifically to facilitate a minimally invasive, robotic approach to the spine.

An object of the devices and system as well as methods described herein is to replicate the desired features of open anterior access with regard to either spinal fusion or motion preservation while limiting the destabilization caused by traditional approaches. The minimal access required for placement of this device aims to minimize complications of traditional approaches such as operative time, blood loss, infections, wound healing and recovery time.

One embodiment of the devices described herein is compatible with surgical robotics. Robotics is an evolving surgical field that aims to significantly minimize the exposure necessary to perform traditional tasks. The application of robotics to spine surgery has thus far been limited to placement of spinal instrumentation. The surgical system described herein aims to utilize the robot as a means for intervertebral disc preparation that would not be possible by a human operator alone. Intervertebral disc preparation is trivial through a large enough annular exposure. However, when the annular exposure is small, complete removal of the nucleus pulposus inside of the annulus is nearly impossible with today's tools. The standard posterior discectomy approach makes it nearly impossible to remove the nucleus pulposus from the opposite side of the disk space particularly along the dorsal portion of the disc space.

Figure 2:
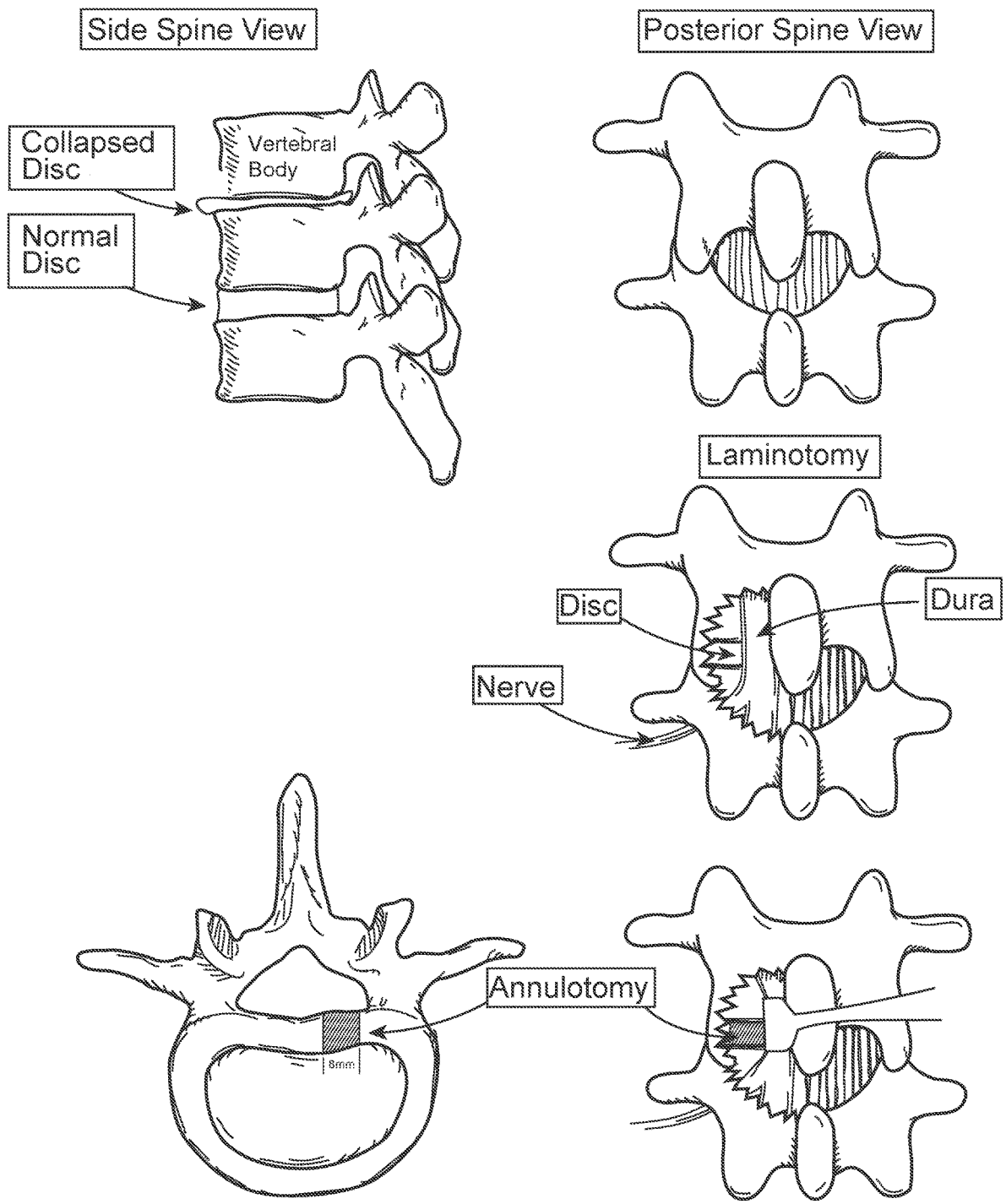
FIG. 2 illustrates a standard hemilaminotomy approach to the lumbar spine for a standard decompressive technique.

The devices and methods described throughout this disclosure draw on the following well described surgical spine techniques; use of surgical planning, use of stereotaxis, use of robotics, and use of ubiquitous surgical approaches such as lumbar laminotomy. In some embodiments the surgery begins with minimally invasive, laminotomy-type exposure of the lumbar spine. One such standard technique utilizes a tubular dilator system. The surgery can also be performed using any known approach to the disc space such as far lateral, anterior, anterior oblique, or transpsoas. The surgery could also be performed percutaneously using electromyography to safely access the disc space. The disc space access provided by these approaches are depicted in FIGS. 1-2.

Devices

Figure 3:
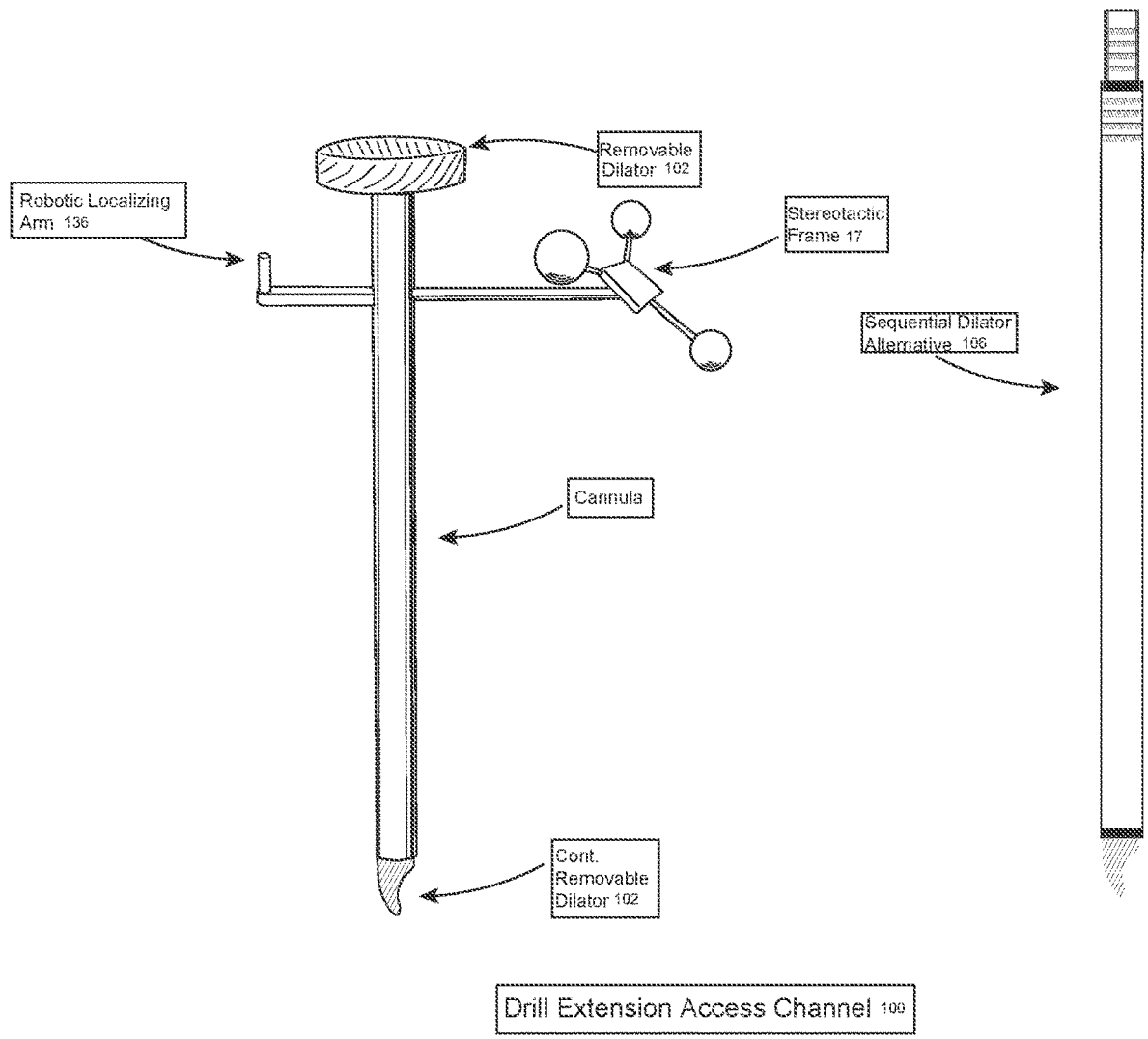
FIG. 3 illustrates a Drill Extension Access Channel (DEAC) with one or optional multiple dilators and with an attached stereotactic frame and robotic localizing arm for holding the DEAC for target localization purposes.
Figure 4:
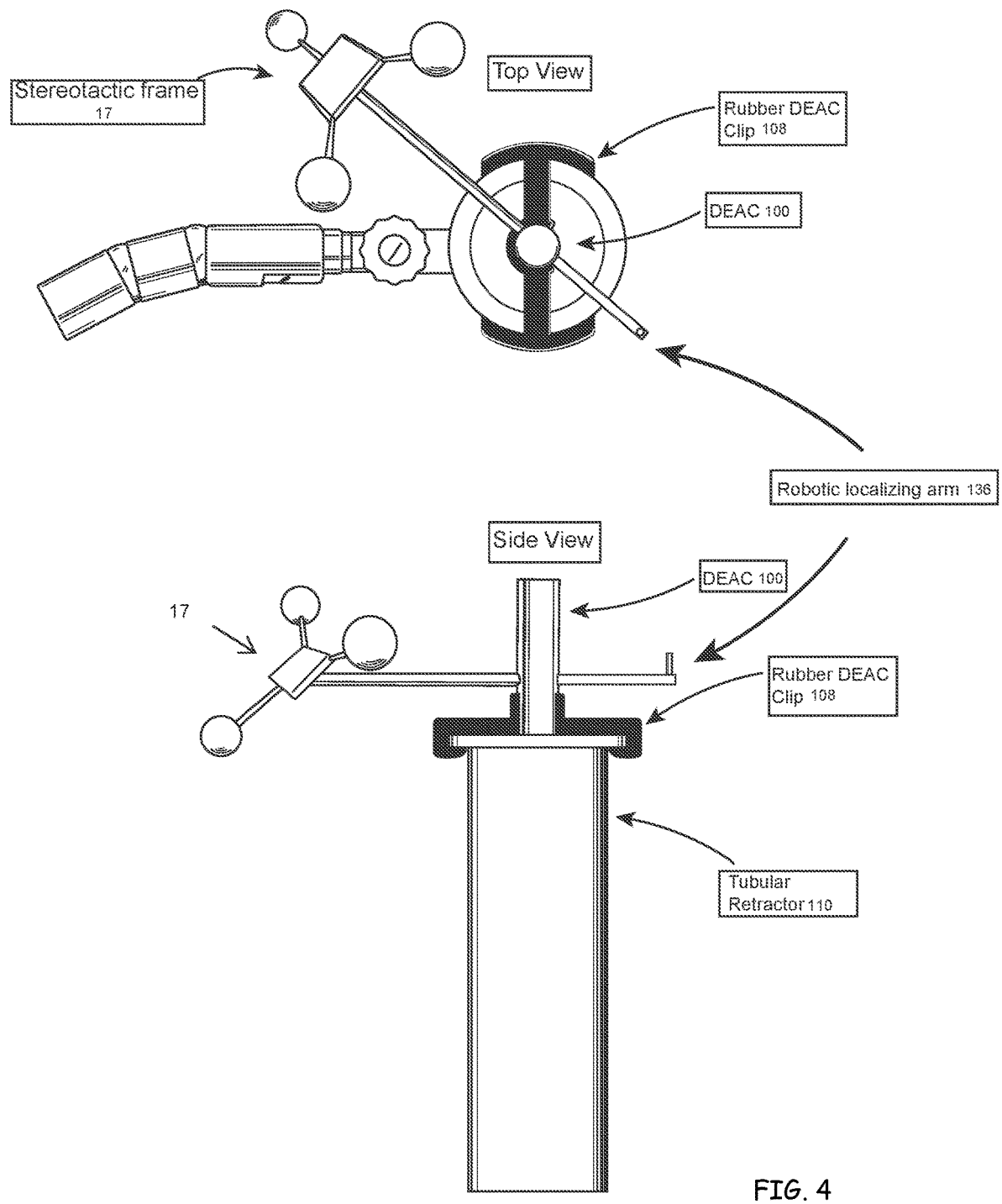
FIG. 4 is a top view of a DEAC used with a standard tubular discectomy retractor and a tube clip shown holding the DEAC in place relative to the tubular retractor according to the present disclosure.
Figure 5:
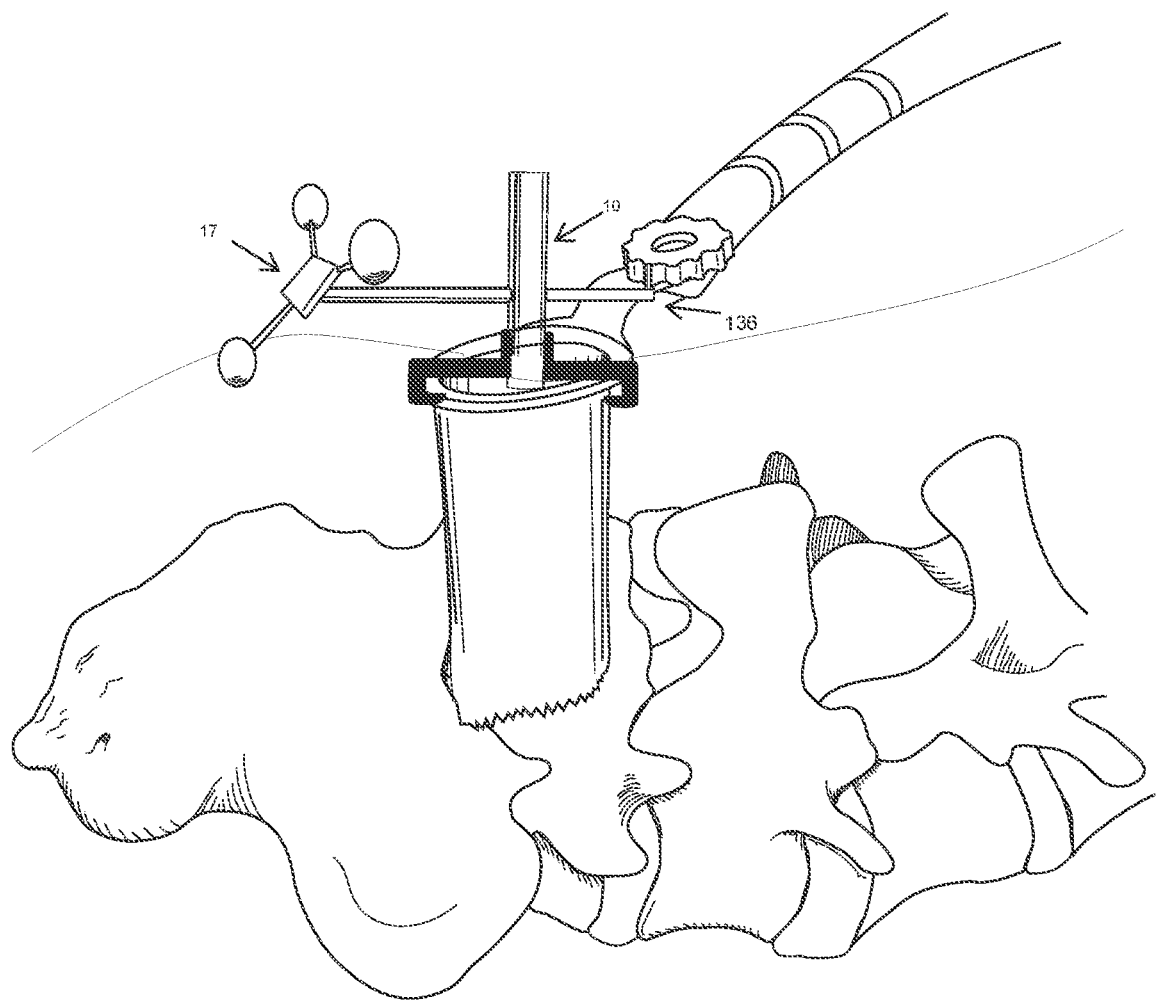
FIG. 5 is an oblique view of a DEAC used with a standard tubular spine retractor.
Figure 6:
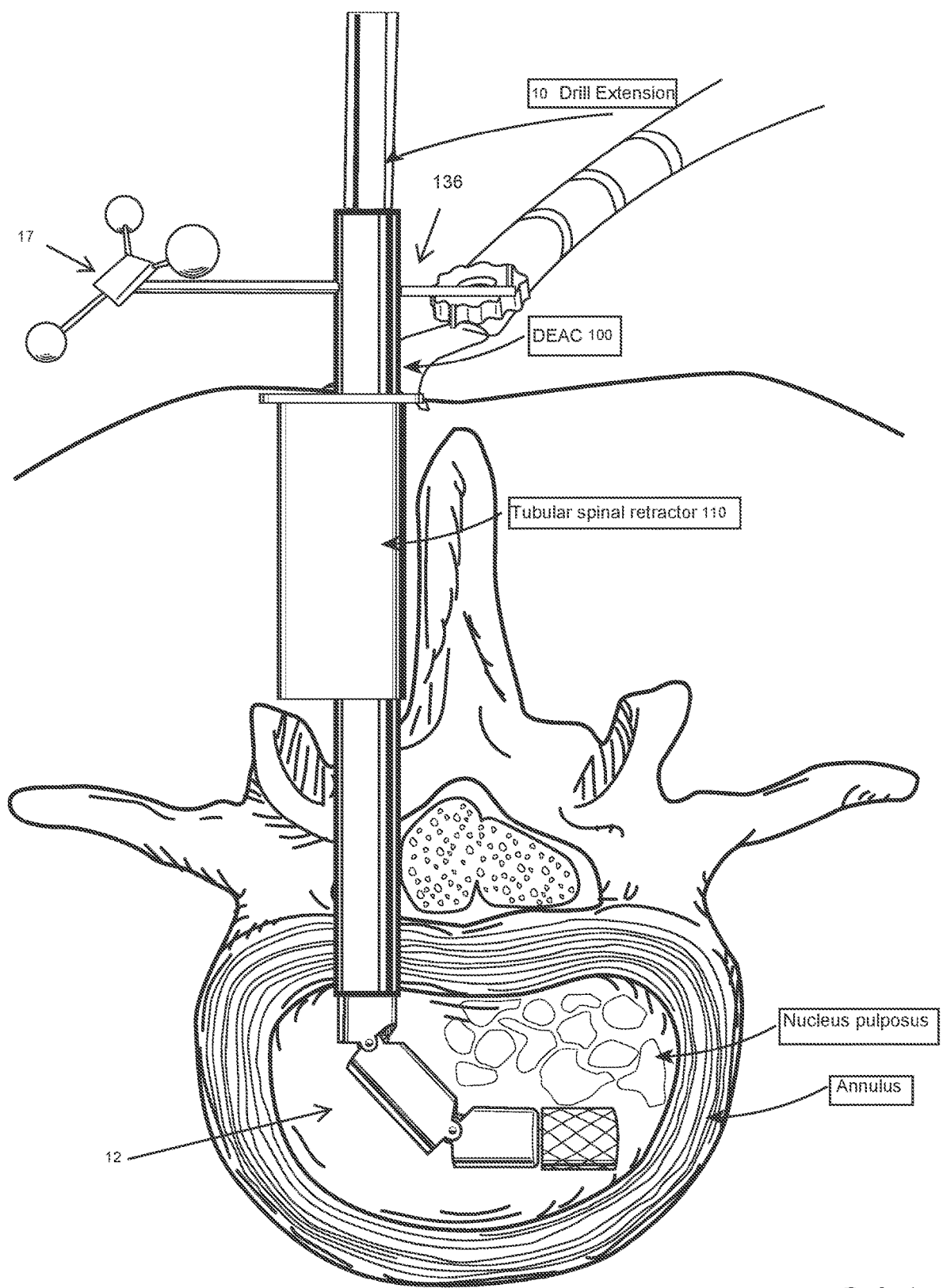
FIG. 6 illustrates a DEAC in place with access to the safe disc space established and an articulating drill extension of the present disclosure working through the DEAC, safely bypassing neurologic structures in the spinal canal as described herein.

DRILL EXTENSION CHANNEL (DEAC). Decompression of neurologic elements is a key need in many lumbar fusion surgeries and a significant limitation of other minimally invasive spine approaches. This technique utilizes standard, ubiquitous spinal decompression approaches. Spinal decompression can be accomplished in standard fashion prior to utilization of the articulating drill extension device to clean out the nucleus pulposus. For example, in a patient with spinal canal stenosis from a disc herniation, the herniated portion of the disc can be removed before proceeding with this method. This is necessary so that neurologic structures can be mobilized adequately to place a drill extension access channel (DEAC) safely into the disc space. An example of a DEAC 100 and its corresponding dilator 102 or dilators 106 is illustrated in FIG. 3. This procedure is illustrated in FIGS. 2 and 4-5. It begins with the surgeon protecting the nerve roots with a nerve root retractor and making an annulotomy with a scalpel as illustrated in FIG. 2. The annulotomy will be sized appropriately to the DEAC 100. The central dilator 102 allows appropriate dilation force to be applied to the vertebral endplates to place the DEAC 100 into the annulotomy. The central dilator 102 can also be a set of serial dilators 106 that allow for incremental dilation of the disc space also shown in FIG. 3. Once dilation is complete, the central dilators 102 are removed leaving the DEAC 100 held in place by the annulus and compression from the superior and inferior endplates of the vertebral bodies as illustrated in FIGS. 4-5.

In the embodiment illustrated, the DEAC 100 has an inner diameter in the range of about 6 to about 14 mm and an outer diameter in the range of no more than about 7 mm to about 15 mm. The DEAC 100 is constructed of a metal such a stainless steel or titanium but any material able to withstand the force applied by the disc space would be sufficient. In this embodiment a dilator 102 such as a central dilator is placed inside the DEAC 100 that is constructed of metal or plastic that is tapered to ensure adequate dilation of the disc space and adequate protection of the adjacent neurologic structures. The central dilator 102 has a cannula and can also be made up of 2-3 serial dilators 106 that are sequentially placed to open the disc space in a more controlled fashion. The DEAC 100 can be held in place by a DEAC-specific flexible clip 108 that spans the tubular discectomy retractor 110, effectively connecting the DEAC 100 to the tubular retractor 110 and its stabilizing arm as shown in FIG. 4-5. This has the effect of connecting the DEAC to the surgical bed as well as the patient.

Once the DEAC 100 is rigidly held in a stable position, a CT or fluorographic study may be obtained to document its stereotactic frame position and orientation to the patient's spinal anatomy. The DEAC 100 can be equipped with a stereotactic frame 17 as seen in FIG. 3. A Y-shaped appendage with reflective spheres in the illustrated embodiment shows a frame 17 that can be modified to match a specific vendor's stereotactic system. Stealth® Workstation or Brainlab® are examples of stereotactic machines that utilize Y-shaped stereotactic instrument frames via infrared cameras to locate the reflective spheres of a patient-attached stereotactic frame and stereotactic-frame-attached instruments in the operating room space. A frame 17 that is attached to the patient's anatomy rigidly, as is the DEAC 100 is in this implementation, allows the stereotactic system to locate an instrument relative to the patient's anatomy. If an instrument with an appropriate stereotactic frame 17 is brought into the system's camera's view, the stereotactic system can display the relationship between the working end of that instrument and its relative location to the patient's anatomy on the patient's imaging study. This is done by showing the surgeon multiple views on the patient's imaging study, such as a CT scan or MRI, the virtual location of the working end of the stereotactic instrument. This works in the same way as some current video gaming systems such as Nintendo Wii® that utilize IR cameras to translate player movements into character actions in the game.

Once the DEAC 100 has been registered by the stereotactic cameras, the stereotactic guidance can be used by a surgical robot to target the DEAC 100 trajectory into the disc space. A robotic arm 36 can then be brought into a position to follow that trajectory. The robotic arm 36 can be used to guide an articulating drill extension 10 into the disc space safely.

The stereotactic system can follow the movements of the articulating drill extension 10 as described in further detail below to virtually account for the area of disc removed and actively change a sliding drill guide limiter(s) 42 and/or a rotating limiter 38 as also described in further detail below, to account for the articulating drill extension end effector 26 position when the stereotactic frame 17 is used as an illustrated in FIGS. 8-11 and as described further below.

To additionally track the patient, some robot systems utilize a fixed pin or localizing arm placed in the patient's bony anatomy that is held by a secondary robot arm. This is another form of stereotaxis that allows the robot to track any patient movements and account for them appropriately. These pins are typically placed in the patient's pelvis. Instead of placing pelvic pins for these robots, this system has a pin like extension 136 off of the DEAC 100 as shown in FIG. 3. This allows for fewer incisions and a less invasive procedure.

Articulating Drill Extension

Figure 8:
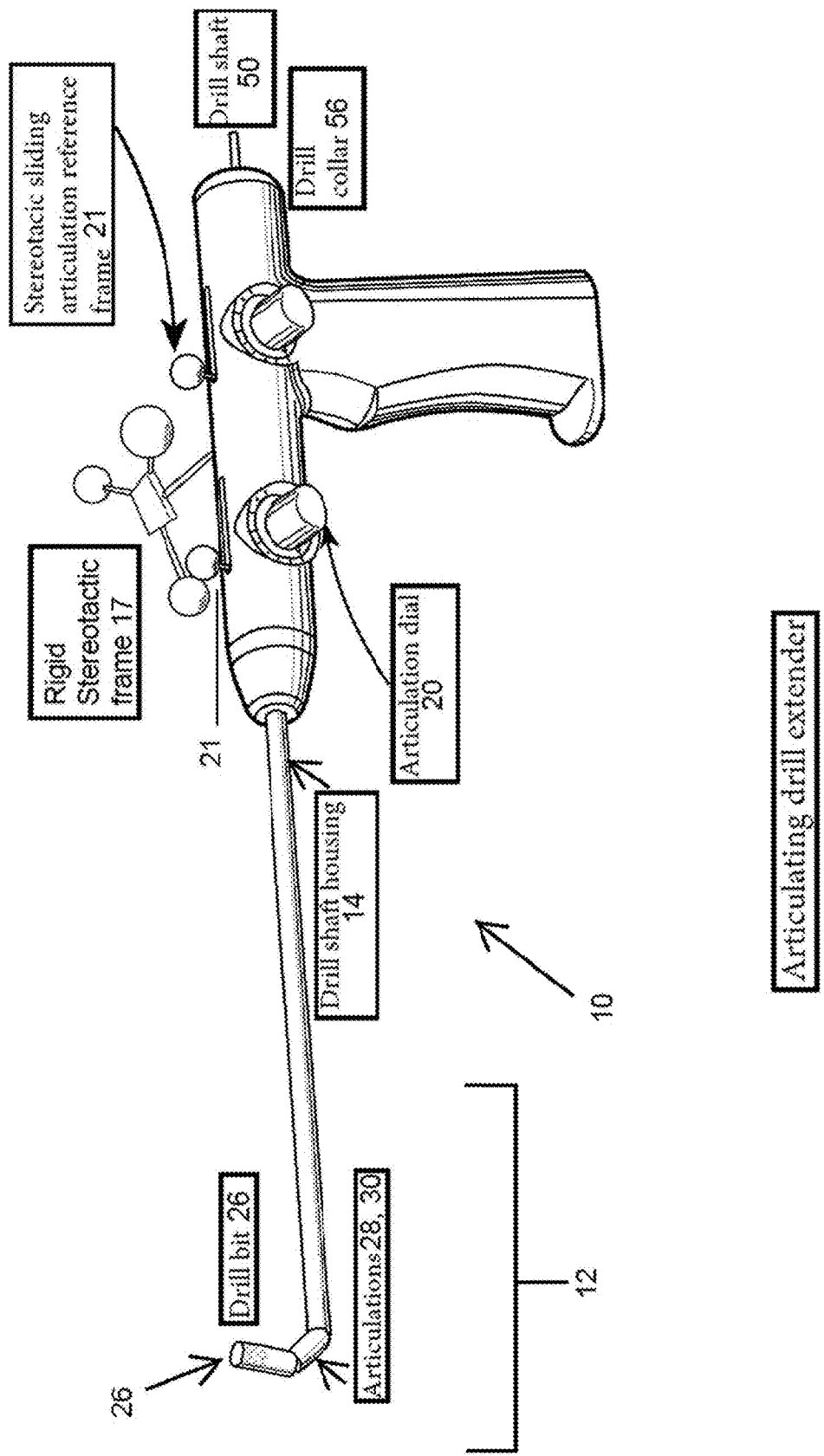
FIG. 8 is an oblique view of the articulating drill extension and illustrating the articulation dials, rigid stereotactic frame, sliding stereotactic reflective sphere posts and spheres used to stereotactically follow the articulating drill extension's associated articulation.
Figure 9:
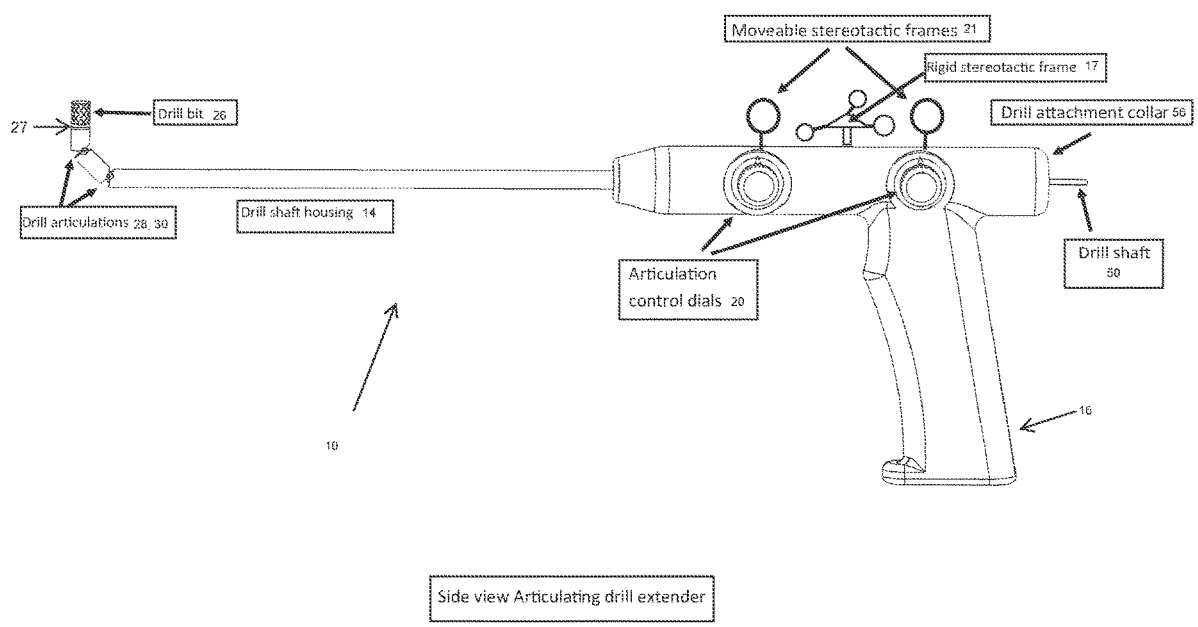
FIG. 9 is a side view of the articulating drill extension.
Figure 10:
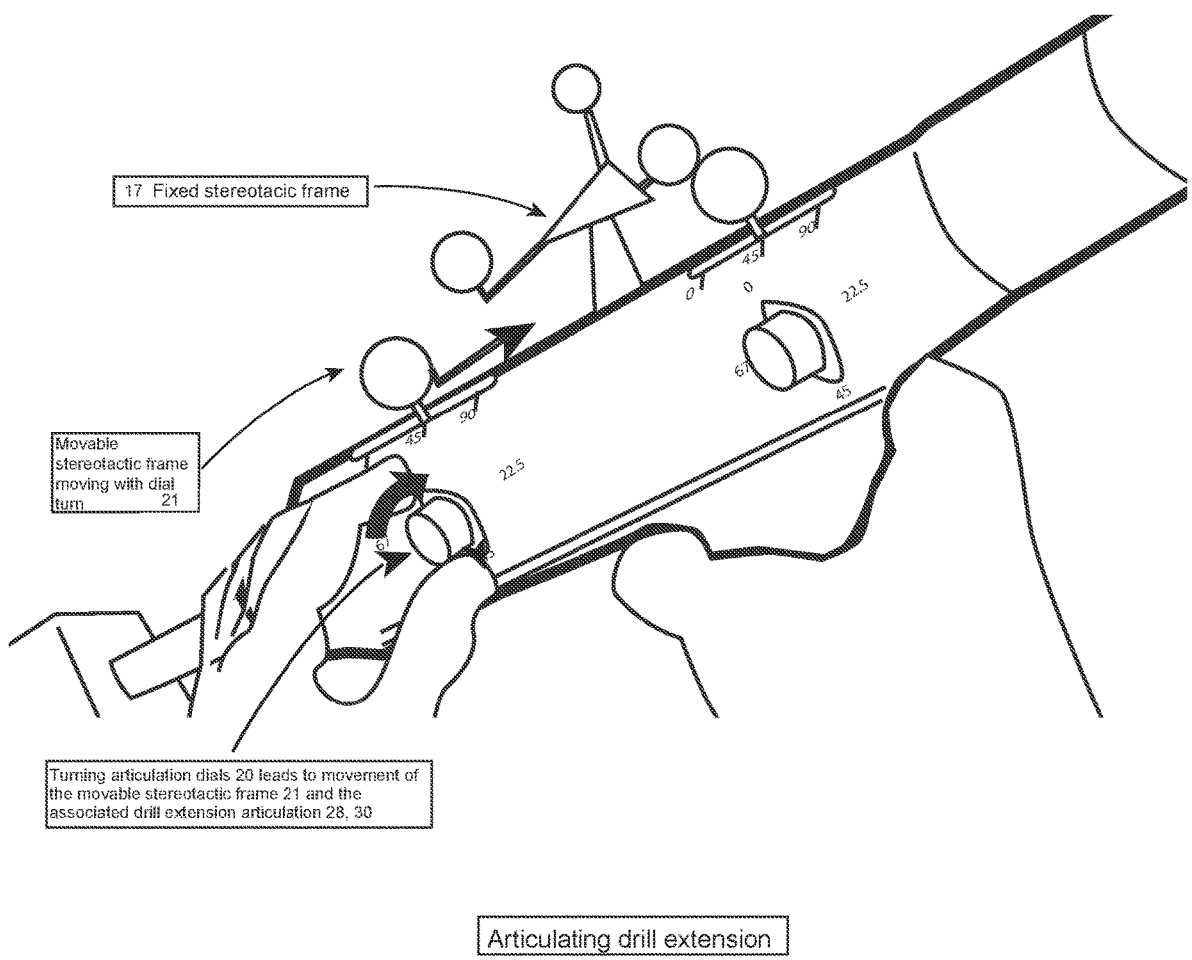
FIG. 10 illustrates an articulation control dial rotation causing linear slide of the moveable stereotactic frame relative to the fixed stereotactic frame.

An articulating drill extension 10 is illustrated in further detail in FIGS. 8-10. In the embodiment illustrated the articulating drill extension 10 comprises a drill shaft 51 extending through a proximal end of a drill extension handle 16. A handle 16 is provided for user control. It some embodiments, a stereotactic frame 17 may be secured to the articulating drill extension handle housing 16.

The drill shaft 51 terminates in a distal end 12 which comprises one or more articulations 28, 30 and respective articulation joints and a drill bit holder 27 for connection with a selected drill bit 26 or end effector. What is meant by the term articulations as used herein are rigid elements that are movable via the articulation joints.

The articulating drill extension 10 also comprises one or more dials 20 to control each of the articulations. The number of dials 20 is equivalent to the number of articulations 28, 30. The articulations include right angle, rotating, and telescoping which through the use of multiple articulations provides a hemispherical range of motion for the drill bit 26. In the embodiment illustrated, there are two articulations 28, 30 and therefore two dials 20. These dials 20 may have torque releases built into a dial-shaft interface to prevent operator over-torqueing. Additional embodiments may obviate the need for dials by letting a robot, for example, control one or more articulation steering cables.

Figure 11:
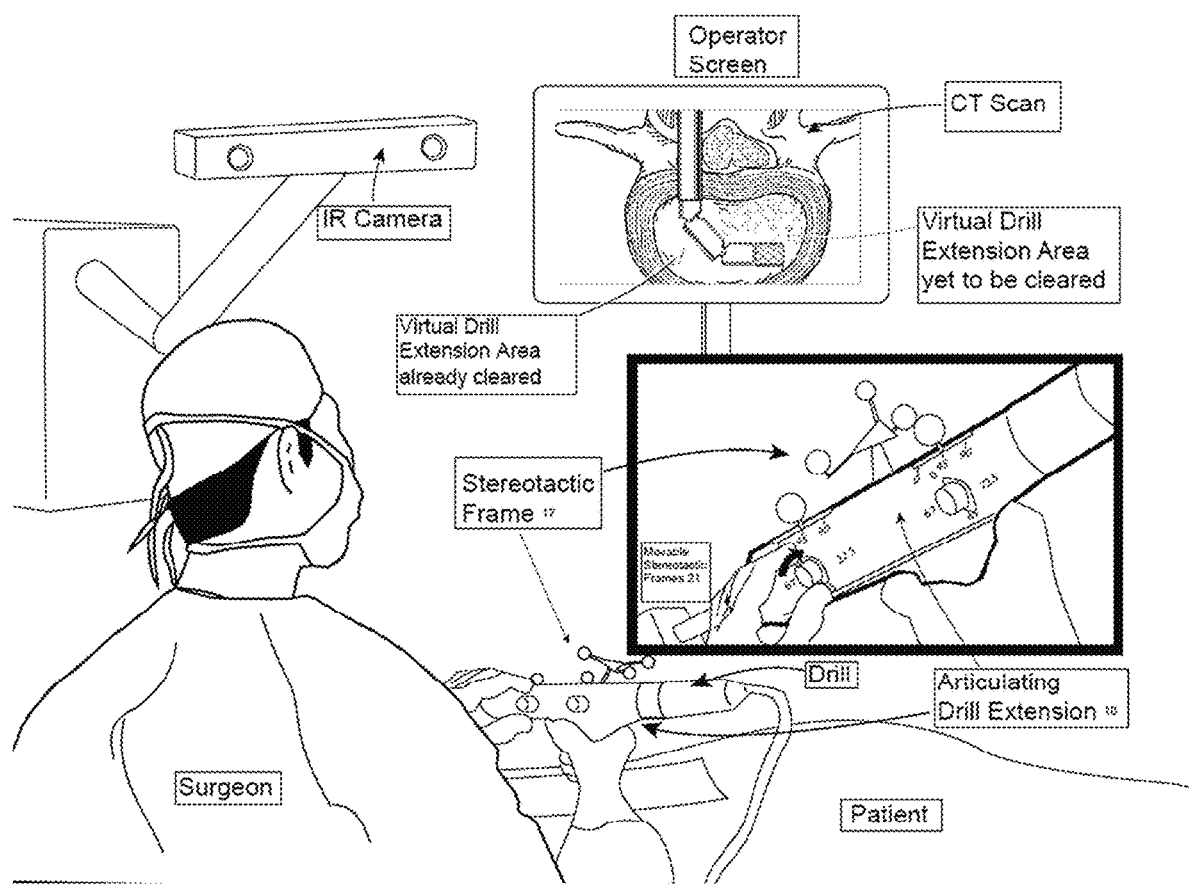
FIG. 11 illustrates an operating setup

Referring now to FIG. 11, which illustrates the use of the dials 20 by a surgeon where the turning of dials 20 results in the articulation's respective stereotactic reflective sphere 21 moving along its slide. Degrees of articulation marked on the dial as shown in FIG. 10 agree with degrees of articulation on the slide. A surgeon is watching the virtual representation of the plan he made for clearing the disc space. As he moves the drill 10 and its articulations 28, 30, the screen shows a corresponding change in the amount of virtual nucleus pulposus remaining to be cleared. The call-out shows greater detail of the sliding stereotactic reflective spheres responding to articulating dial turns.

Each dial 20 controls a steering cable 33 that runs the length of a steering channel 32 within the articulating drill extension shaft housing 14 and terminating at the appropriate respective articulation 28, 30. The steering cable 33 is attached to a steering control cam on the articulation joint. The side of the articulation 28, 30 with the steering control cam attached will henceforth be referred to as the control side. The steering cables 33 run in-line with the articulation 28, 30 along the drill shaft housing 14. In the embodiment illustrated there is a lateral shaft, loops, or grooves running along the shaft housing 14 to hold the steering cables 33 in a stable orientation with respect to the articulation cam 139. The steering cables 33 are attached to the dials 20 on the drill extension handle housing 16 with a cam on the end of the dial shaft. This cam may be under spring tension to ensure the appropriate tension is maintained for the cable steering system to function properly.

Figure 12:
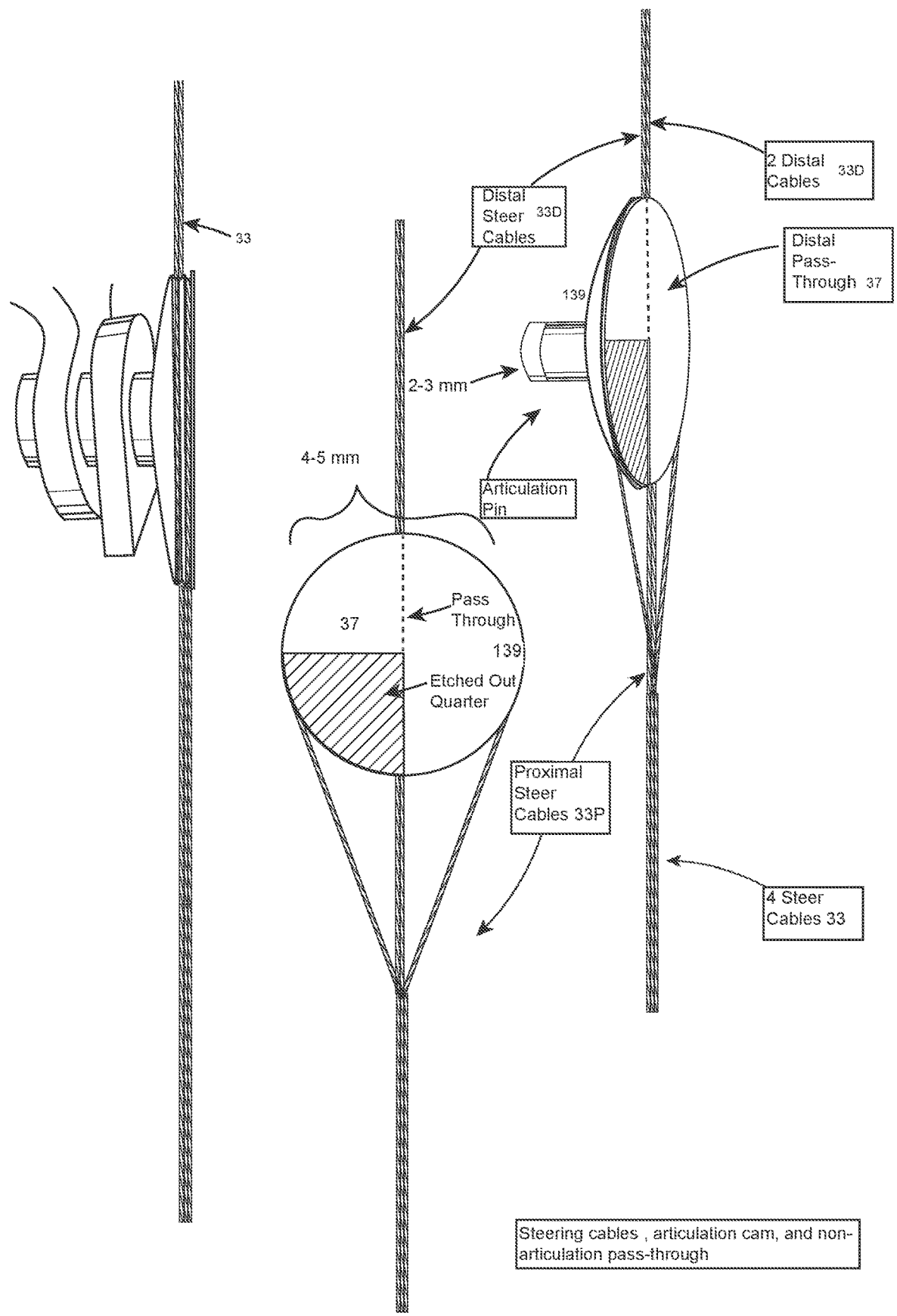
FIG. 12 illustrates a steering cable articulation interface where a proximal articulation design is illustrated with proximal steering cables action on articulation cam and distal steering cable pass-through at the articulation designed specifically to keep the length of the distal articulation constant.
Figure 13:
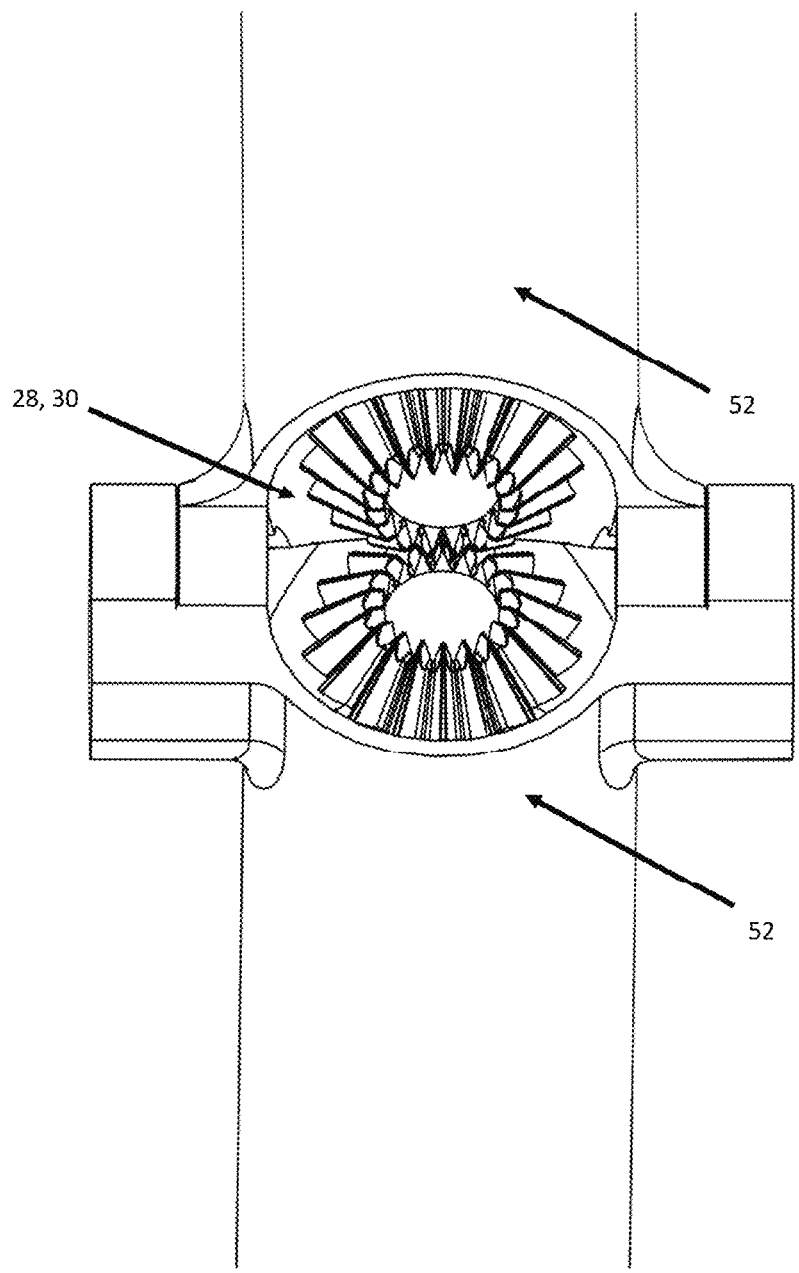
FIG. 13 illustrates solid drill shaft articulation bearing gears.

Referring now to FIG. 12, the distal articulation steering cables 33D may require an accommodation 37 to pass by non-actuated, proximal articulations. This may be accomplished by passing the distal cable 33D through the articulation 28, 30 opposite the proximal articulation's control side. There is a pass through, or tunnel, built into the proximal, non-control articulation to allow stable passage of the distal articulation steering cable 33D. The distal articulation steering cable 33D must be held in place while the proximal articulation cables 33P control the articulation. The distal steering cable 33D slides freely within or through the etched out quarter as the proximal articulation ranges from 0 to 90 degrees, while remaining relatively confined in-line with its control articulation. By keeping the steering cables 33 in-line with their control articulation, distal articulations can be individually tensioned while not affecting the tension on the more proximal articulations.

Controls may be fixed to the drill extension handle housing 16 that move stereotactic reflective spheres 21 along slides to reflect the drill extension's articulation angle as the articulation control dial 20 turns. This allows stereotactic navigation software to virtually follow the articulation positions of the articulating drill extension 10. The position of the reflective sphere along its slide may be calculated by the stereotactic software relative to the fixed stereotactic frame 17 that is also attached to the articulating drill extension handle housing 16. When the articulation control dial 20 is turned, the articulation-specifying stereotactic reflective sphere 21 will move to a slide position that reflects the new angle of the corresponding drill extension articulation.

The articulating drill extension shaft 14 is a housing that may be constructed from materials such as titanium, stainless steel, aluminum, plastic, carbon fiber, or combinations thereof. The shaft housing 14 wall thickness may be between about 0.2 mm and about 2 mm. The shaft housing 14 length may be between about 10 cm and 50 cm including any end articulations 28, 30, but not including the articulating drill extension handle housing 16 or drill itself. An outer diameter of the shaft 14 may be between about 7 mm and 15 mm. An inner diameter will vary by outer diameter and wall thickness selected.

Figure 14:
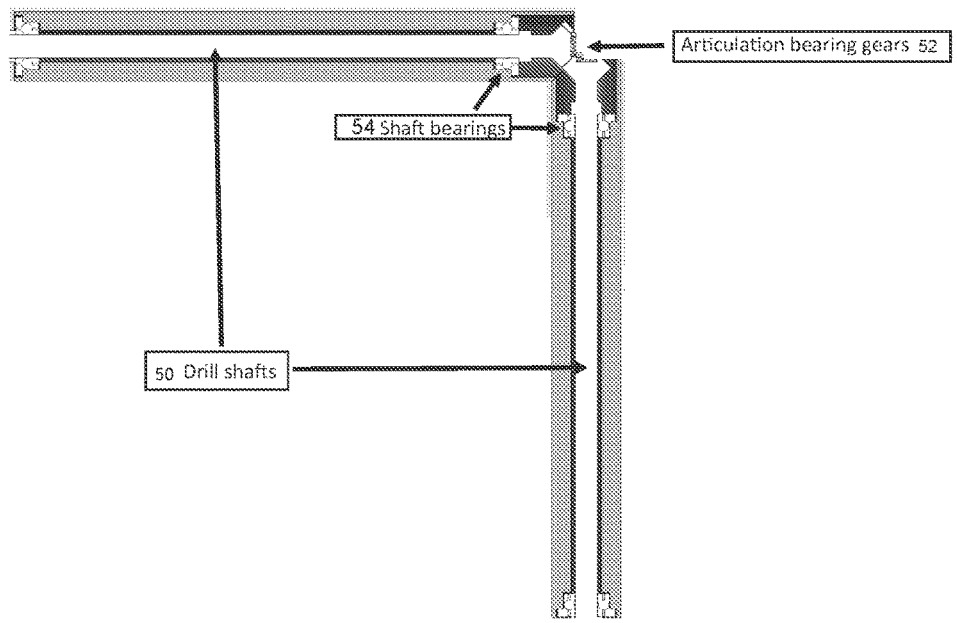
FIG. 14 is a cutaway view of the articulating drill extensions shaft housing showing internal components such as articulations, steering cables, drill shaft, drill shaft bearing gears, shaft bearings, inner shaft housing sleeve with steering cable channels.
Figure 14:
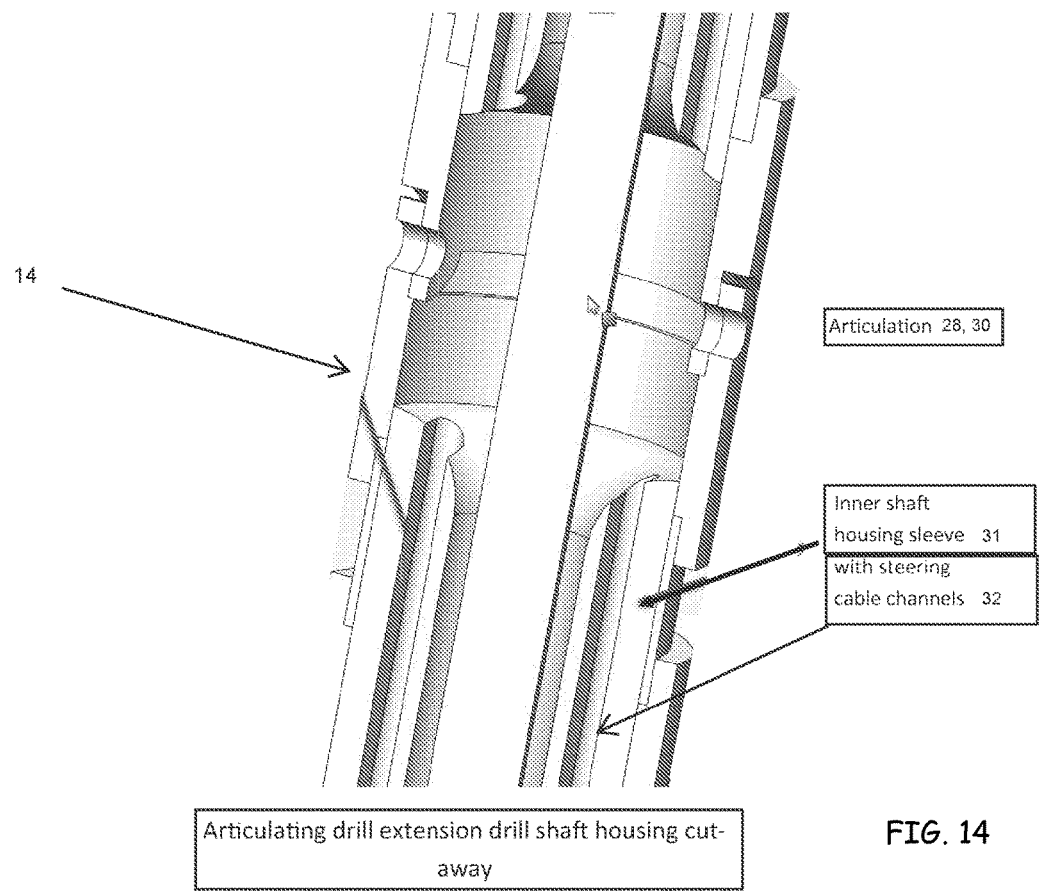

Inside the shaft housing 14 is a shaft mechanism 50 as illustrated. The shaft 50 itself may be a solid shaft made of either stainless steel or titanium contained within the housing 14. A diameter of the main shaft 50 may be between about 2 mm to about 10 mm. The shaft runs from the proximal end of the drill extension 10 where the drill itself can be hooked onto the shaft 50 at the end. Variable drill housings and shaft connections can be manufactured to hold drills from a variety of manufacturers onto the drill extension shaft 50. These housings 16 may be constructed with dimensions to fit various manufacturers' drills, and it is also contemplated that the housing may also be compatible with robotically controlled drills. The shaft 14 contains enclosed ball bearings 54 at the proximal and distal ends of the shaft 14 to allow for smooth articulations at high RPMs. The shaft 50 terminates in a distal 45-degree bevel gear 52 that has been specifically designed to function at all angulations of the two shafts 50 between 0 and 90 degrees. This shaft gear 52 is a novel bevel gear design specifically designed to accomplish this. The 45-degree bevel gear 52 allows for multiple 90-degree articulations along an otherwise solid shaft 50 for optimal torque delivery. A distal shaft 50 continues after its proximal bevel gear 52 to terminate at its own distal bevel gear 52. There are bearings 54 before each bevel gear 52 along the shaft 50 as illustrated in FIG. 14.

In the embodiment illustrated, referring to the proximal section of the drill extension 10, the proximal gear shaft 50 is a 3 mm outer diameter shaft that is a minimum of 12" long, with a 45 degree, 96 diametrical pitch, bevel gear 52 on the distal end of the shaft 50. The proximal end of the shaft 50 contains the features necessary to the drill attachment collar 56. The bevel gear 52 is attached to the long shaft via a threaded post with right hand threads. When the drill is rotating clockwise it continues to tighten the shaft 50 to the gear 52. A medical grade thread locking liquid adhesive may be used as a redundant means of keeping the assembly intact.

The articulating end 12 of the articulating drill extension 10 comprises articulations 28 and 30. Referring back to FIGS. 8-9, the articulations 28, 30 allow for hemispherical movement of the attached drill bit 26. The midsection 24 of the articulating end 12 of the articulating drill extension 10 comprises dual bevel gears 52. This section is in the range of about 9 mm to about 25 mm long from pivot point 30 to pivot point 28. There is a 45-degree, 96 diametrical pitch bevel gear 52 on each end of the shaft 50. The midsection 22 may be manufactured out of two halves which also contain a threaded post attachment method in the manner of the same on the proximal shaft 50.

The distal section 24 of the articulating end 12 has a fitting 27 for a detachable bit 26 on its distal end and a bevel gear 52 on the proximal end. The distal section 24 is in the range of about 10 mm to about 30 mm long. The distal section 24 of the assembly has a 15 mm long drill bit 26 that is the same out diameter as the outer shaft housing. The proximal end of the assembly has a 45-degree, 96 diametrical pitch bevel gear 52. The two halves attach with a threaded stud and thread locker as the other two sections described above.

In a double articulation embodiment of the articulating drill extension 10 there is an interarticulation or middle articulation segment 22. The distance of the middle articulation segment in a two-articulation implementation is in the range of about 1 cm to about 3 cm. The shaft housing for this segment terminates in articulations at both ends 28, 30 with the proximal end having a distal articulation and the distal end of the segment having a proximal articulation. This makes manufacturing the short shaft that resides in the interarticulation housing 22 difficult as the gears are higher in diameter than the inner diameter of the bearings to be used. The shaft 50 itself in this embodiment is constructed in two parts: the proximal gear 52 terminates in a male threaded pattern and the distal gear 52 initiates with a female threaded pattern, which runs about 1 cm to about 3 cm of the shaft 50 length before terminating with its distal gear 52. Bearings 54 may be affixed before final assembly. The shaft 50 may then be laser welded at its union or, because the drill rotates in one direction, clockwise for example, the threading can be left to hold the shaft together if it is made to tighten in the same direction.

The distal segment 24 of the drill extension may be a 0.5 cm-4 cm segment with a distal articulation 30 at its proximal end and a sealed bearing cap at its distal end. The shaft inside the housing will initiate with the bevel gear 52 design described herein and terminate with a drill bit 27 or a shaft designed specifically to accommodate replaceable drill bits 26. There may be a bearing 54 after the bevel gear 52 and a sealed cap and bearing 54 at the distal end of the shaft housing 24. The distal shaft in a replaceable drill bit system may terminate in a hexagonal or square configuration of the shaft with a distal notch to accommodate a locking device contained in the drill bit 26 itself.

In operation of the articulating drill extension 10, the dials 20 located on the drill extension handle housing 16 turn their associated articulation 28, 30 a ¼ degree for each one degree turn of the dial 20. Therefore, the dial 20 must be turned 360 degrees to achieve a 90-degree articulation angle. The corresponding movement of the stereotactic reflective sphere on the handle housing 16 will reflect a linear distance that the stereotactic software equates to each degree of articulation. For example, if the slide is 30 mm in length, every millimeter the reflective sphere moves along it would represent 3 degrees of drill joint articulation.

As disclosed above, the articulating drill extension 10 may be used with a robotic arm 36. Once the DEAC 100 has been registered by the stereotactic cameras as described previously above, the stereotactic guidance can be used by the robot to target the DEAC 100 trajectory into the disc space. The robotic arm 36 can then be brought into a position to follow that trajectory. The robotic arm 36 can be used to guide the articulating drill extension 10 and articulating end 12 into the disc space safely. The robot can utilize a very small annular opening for disc space access thereby limiting any destabilization of the disc space. The disc removal may be performed with a robotic appendage that utilizes a hollow articulating arm with a drill shaft 51 running through the central portion. The arm utilizes the drill bit 27 to morstelize the disc, remove endplate cartilage and prepare a bleeding bony surface if a fusion is the goal of surgery. The drill shaft can be connected to existing drill power sources or to a new drill device controlled by, for example, an operative robot. The articulating drill extension described above can be adapted for use with the robotic arm such that at each articulation 28, 30 a new solid drill shaft interfaces with the previous to allow transmission of torque any at articulation angle between 0 and 90 degrees.

Figure 7:
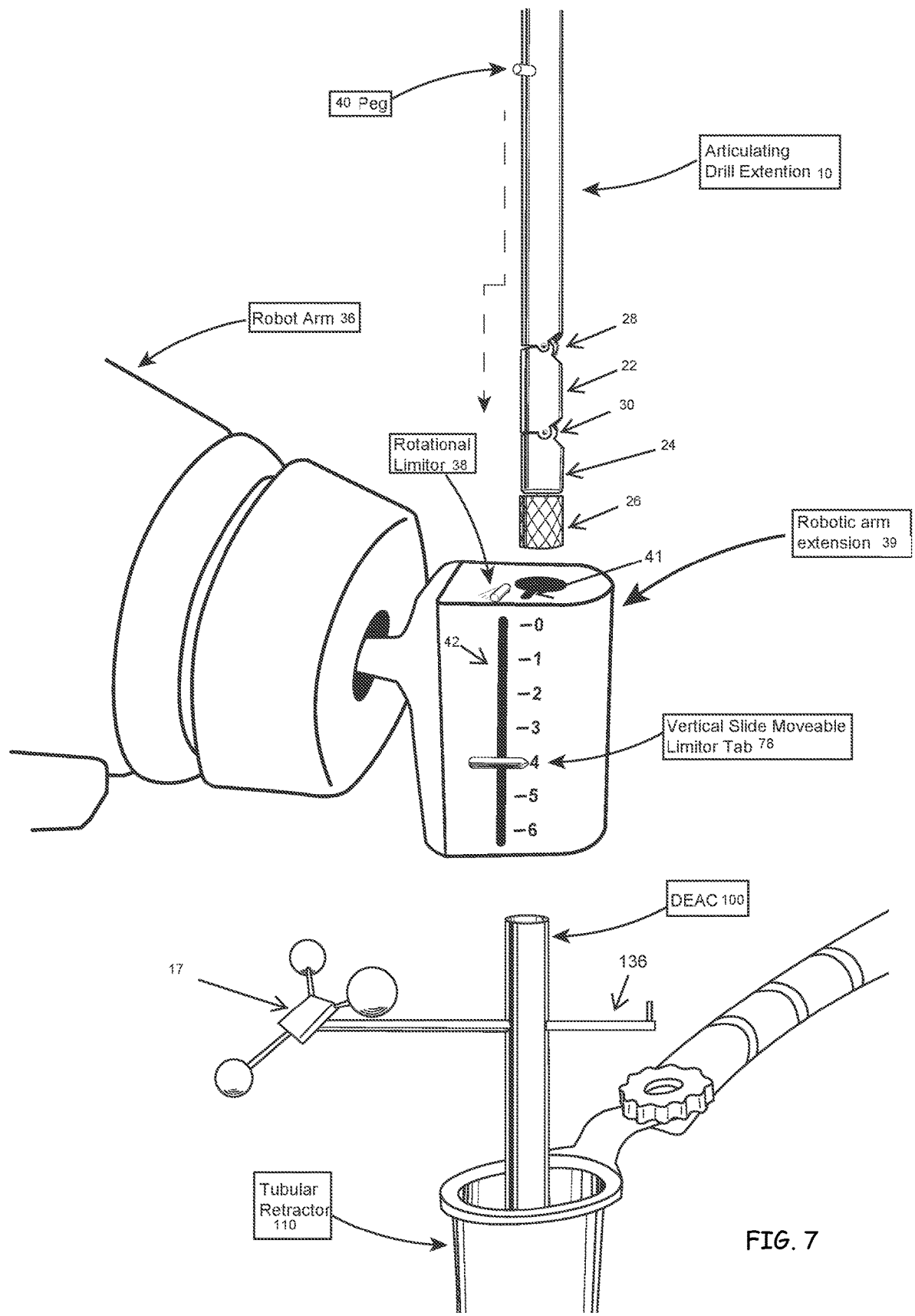
FIG. 7 illustrates an articulating drill extension sliding guide in an embodiment as a new robotic arm extension with a diagram illustrating a peg on the articulating drill extension drill shaft housing as movable into the sliding guide.

As discussed above, the articulating drill extension 10 may be controlled by a surgeon or a surgical robot 36. In one embodiment where in the drill extension 10 is controlled by a surgical robot 36, the drill shaft is connectable to a robot arm 36 directly via a connection mechanism 39 also referred to as a robot arm extension 39 as illustrated in FIG. 7. The robot arm extension 39 may comprise the sliding guides 38, 42 as briefly discussed above. In further detail, the sliding guide 42 limits the movements available to the surgeon using the articulating drill extension 10. This allows for the protection of all structures adjacent to the patient's disc space and prevents the surgeon from drilling through the annulus in any given direction. In the embodiment illustrated the sliding guide 42 of the robotic arm 36 or is otherwise a working robotic arm extension 39 that actually attaches to the robotic arm which allows a fixed motion path in and out of the DEAC 100. It is also contemplated that the sliding guide 42 is integral to or actually forms a new sterile robotic arm extension 39. A drill extension shaft 14 may have a peg 40 or set of pegs that connect into the guide 42 via connection with a corresponding slot. The guide 42 may be slotted on its inner cannula to restrict how far in or out the drill extension is able to move.

Referring to FIG. 7, a length of a slot 42 on the sliding guide 39 can be varied by one or more control tabs 78 and the surgeon or control robot may select the length of the slot 42 based in part on the specific anatomy of the patient in order to limit inward, outward, and/or rotational movement of the articulating drill extension 10. Limiting mechanisms on the sliding guide 42, referred to also as limiters, may comprise a vertical and horizontal bar that traverse the peg slot 41 of the sliding guide 42. Inward movement of the vertical bar or bars would result in rotational limits to the articulating drill extension 10. Up or down movements of the horizontal guide then may limit the depth of the user could achieve with the articulating drill extension 10. The height of the robotic arm 36 in this example controls the superficial limit impose on the articulating drill extension 10. In the embodiment illustrated, the articulating drill extension 10 is placed in the patient and removed from the patient when the arm is in its non-articulated state that is, when there are no bends in the arm.

The drill shaft can be held in a fixed trajectory by the robotic arm 36 and operated by a human operator or the drill arm can be completely controlled by the robot. The articulating drill extension 10 has applications in other surgical areas. Orthopedic operations, such as knee or hip replacements, are examples of procedures where this device would find wide usage. The articulating torque delivery of the device can find application to other areas outside of medicine as well given its small size, proximal control of distal action and unparalleled ability to deliver high torque remotely to a constrained space.

Hydrostatic Endplate Elevator

Turning now to FIGS. 15A-15D, a hydrostatic expander for preparing a disc space is illustrated at 70. The hydrostatic expander 70 is used to elevate the discs or endplates relative to each other before or after the disc removal takes place. This is an important step in a fusion surgery. Restoration of normal anatomic alignment is performed by expanding a collapsed disc space. Open techniques for this procedure allow for invasive devices such as interspinous spreaders to forcibly spread the vertebrae apart. This opens a disk space that has collapsed from degenerative disease. This is a problem for all minimally invasive disc surgeries as there is no good option to force the disc space back into its normal anatomic alignment with minimal anatomic exposure. For that reason, we describe here a hydrostatic device to evenly apply pressure to the endplates and thereby restore anatomic alignment.

Figure 15:
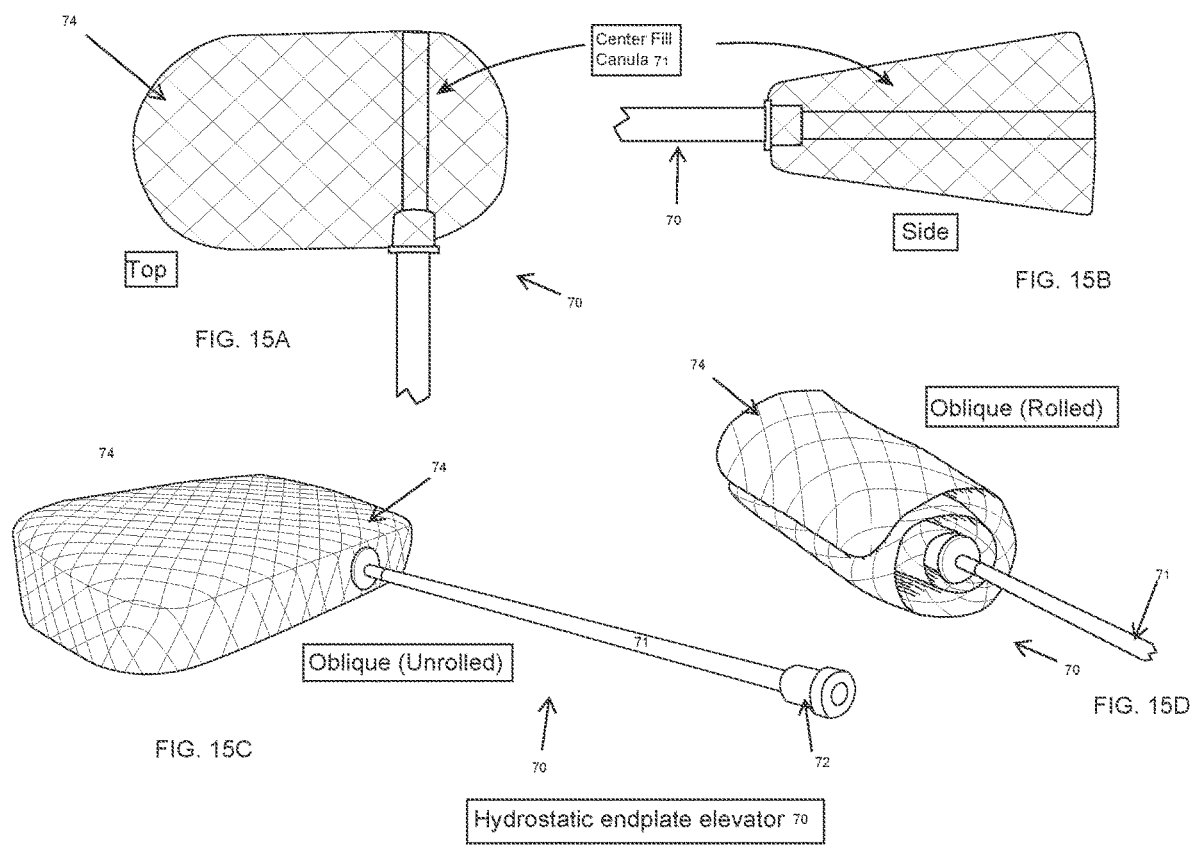
FIGS. 15A-15D illustrate a hydrostatic disc elevator device and its attached cannula as described herein.
Figure 16:
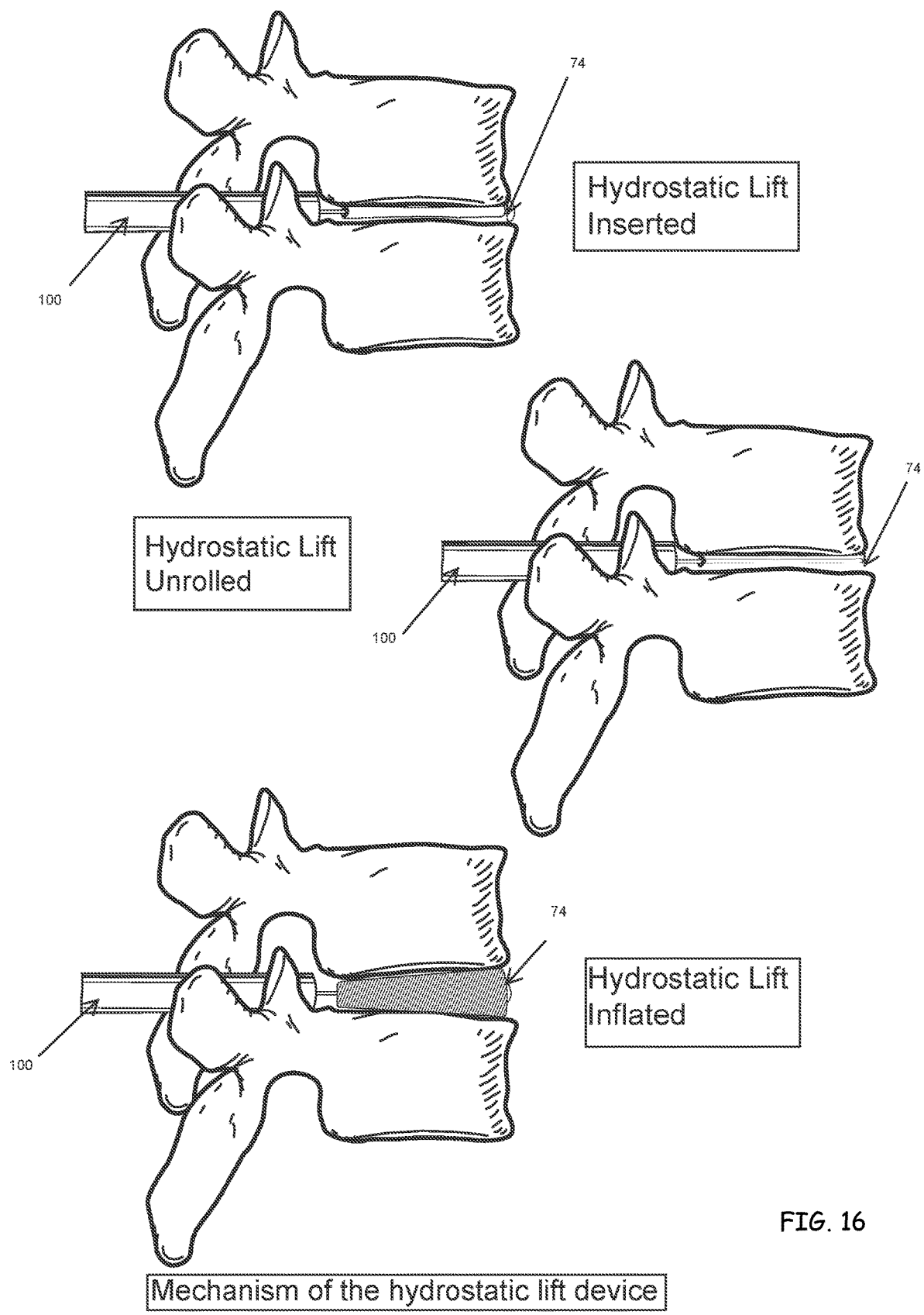
FIG. 16 illustrates the hydrostatic disc elevator placement and use.

The device 70 has a pre-selected footprint based on the disc area to be cleared by the articulating drill extender 10. The surgeon also chooses the height of the hydrostatic expander 70 as part of the preoperative surgical plan or during the actual surgery. The pre-selected shape and size could also correspond to the desired final implant to be utilized. The expander itself 74 is rolled in a collapsed state around the inserter/fill cannula 71 as illustrated in FIGS. 15D and 16. This is accomplished in one embodiment by utilizing a nitinol skeleton or variance of the thickness of a latex, silicone or polyurethane water-tight enclosure. The nitinol provides shape retention under pressure and can assist in rolling and unrolling of the device expander 74. By selecting the correct nitinol alloy the wire can be formed in a rolled configuration at room temperature and straighten into the endplate elevator's predetermined configuration at body temperature as illustrated in FIGS. 15A-16. Once the rolled device 74 is passed into the disc space it can be unrolled and it is then filled, utilizing hydrostatic pressure to achieve appropriate restoration of the patient's anatomic alignment as illustrated in FIGS. 15A-15B. The hydrostatic expander 70 may have the appropriate lordosis, kyphosis or lateral corrections built into it. The patient's own annulus then acts in its natural function as a counter force to the elevator 70. The elevator 70 can be specifically manufactured for a predetermined surgical plan. This device is of great utility in typical degenerative disease cases but most importantly in degenerative scoliosis cases. In these cases, the preoperative surgical plan becomes paramount. The hydrostatic expander 70 can be manufactured specifically to conform and repair anatomic malalignments prevalent in severe degenerative cases.

In further detail, the hydrostatic expander 70 comprises a plastic tube 71 with a male IV port 72 on its proximal end and a preformed collapsible/openable end effector 74 found on a distal end as illustrated in FIGS. 15A-15D. Nitinol wire may incorporated into a membrane 74 of the hydrostatic expander 70 such that walls are incorporated into the end effector 74 to direct flow and expansion. The membrane 74 has a predetermined shape and is configured to allow for controlling the shape of the end effector 74 to control expansion of the disc space with utilization of the proper lordosis or kyphosis. The membrane 74 may be constructed of silicone, latex, graphene, polyurethane, like materials or a combination thereof.

When the hydrostatic expander 70 is inserted into the disc space as illustrated in FIG. 16, the hydrostatic elevator 70 can be "unrolled" and the nitinol wire itself may help obtain the proper orientation of the hydrostatic elevator 70 in the disc space prior to the expansion of the hydrostatic elevator 70. The hydrostatic disc elevator 70 is designed to handle high pressure up to 700 atmospheres. It is removed by rolling the device back into its pre-deployment configuration and extracting it through the drill extension access channel 100.

During surgical procedures, after the disc space has been expanded as described above, the DEAC 100 can be removed. At this point a final implant 200, as described below, can be placed. If a fusion is desired the implant described for this implementation is an expandable device that is pre-configured to a very specific shape. This makes this process different from other approaches such as Spineology's® amorphous bag filling implants. In the implant described herein, standard intervertebral implant sizes or sizes similar to the hydrostatic elevator and configurable implant sizes are used. This allows for preoperative surgical planning to define and manufacturer on-demand implants.

Implant Selection

Figure 17:
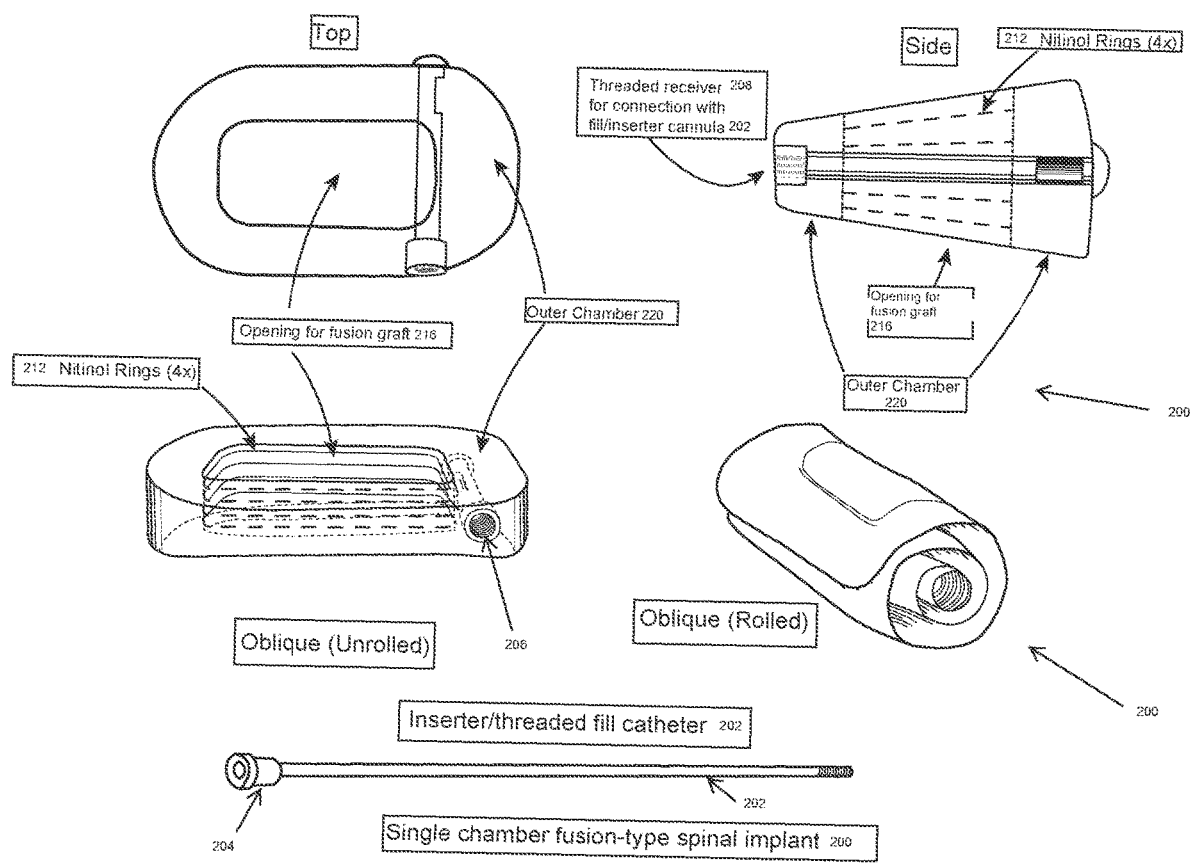
FIG. 17 illustrates a fusion implant device design according embodiments described herein.

Referring now to FIGS. 17-21, an appropriate implant 200 is selected based on the volume and dimensions of the hydrostatic expander 70 that is to be used. The disc implant 200 is a shaped, collapsible container designed around a rigid central access channel 206. The container is made of thin, pliable material such as silicone, latex or polyurethane that can be completely collapsed and rolled around the central access channel 206. The central access channel 206 is in the range of about 2 mm and 10 mm in diameter. The central access channel 206 may have a threaded portion 208 for connection with the fill or inserter cannula 202. This implant 200 is not designed to have expandable walls. In one implementation as shown in FIG. 17, nitinol wires or rings 212 may be used to maintain the wall shape of the device 200. In one embodiment, the wire frame 212 would be used to conform to the device's inner graft wall and the posterior cross-support. This allows for a taller anterior portion of the ellipsoid implant. This replicates the anatomic lordosis of the disc space.

Figure 18:
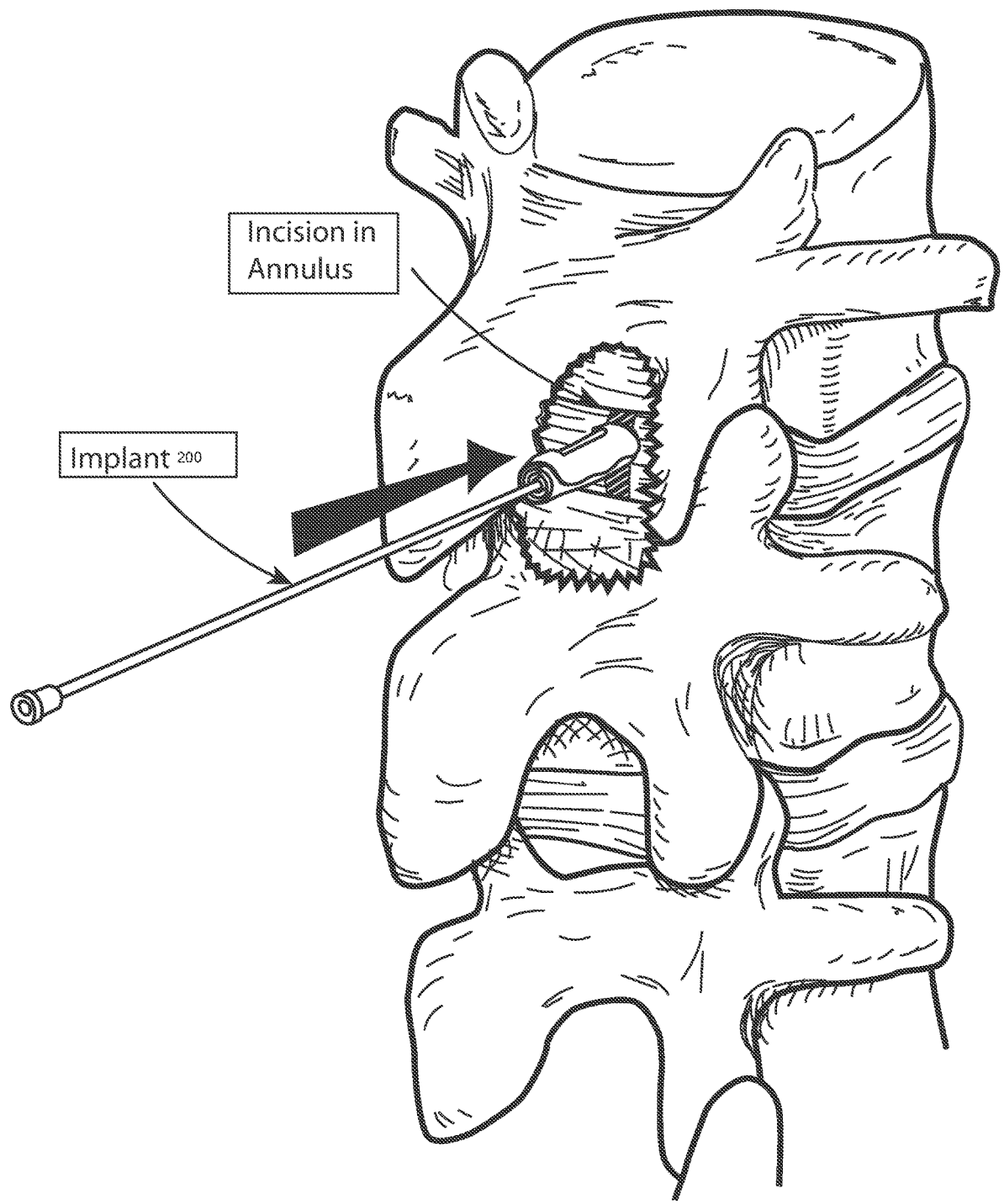
FIG. 18 illustrates the fusion implant device placement.
Figure 19:
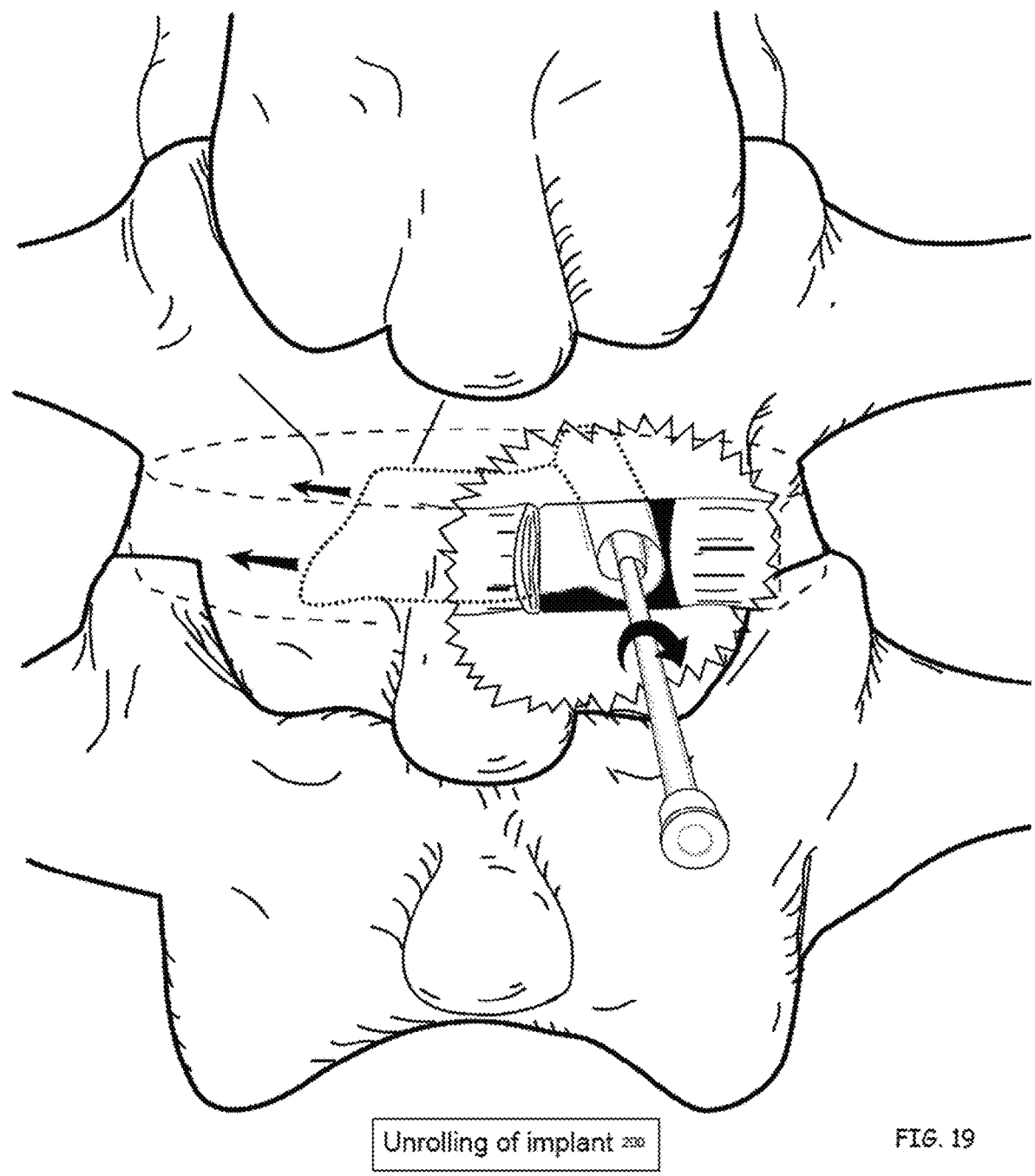
FIG. 19 illustrates the fusion implant device unrolling.
Figure 20:
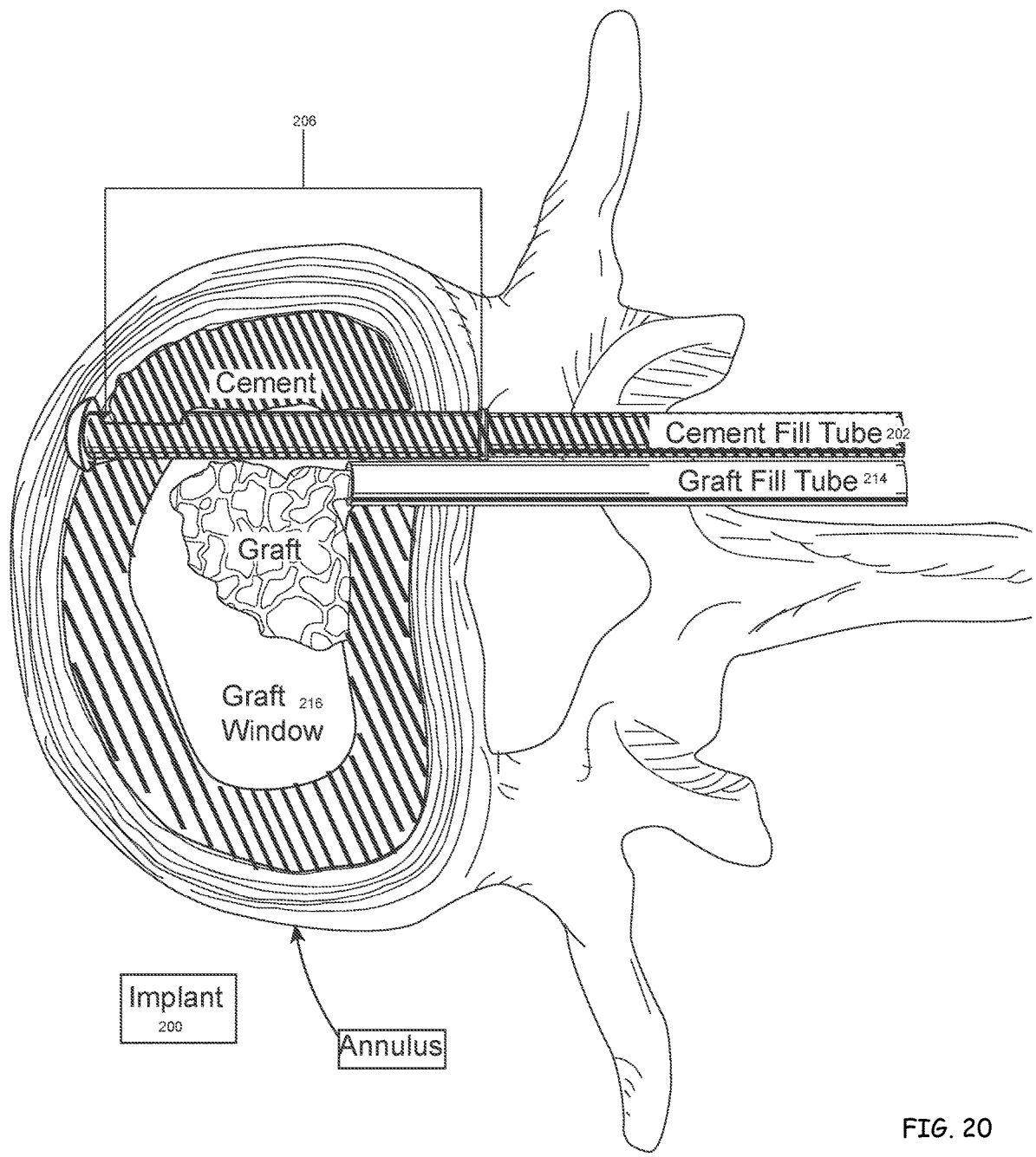
FIG. 20 illustrates the fusion implant device filling with graft window filling.
Figure 21:
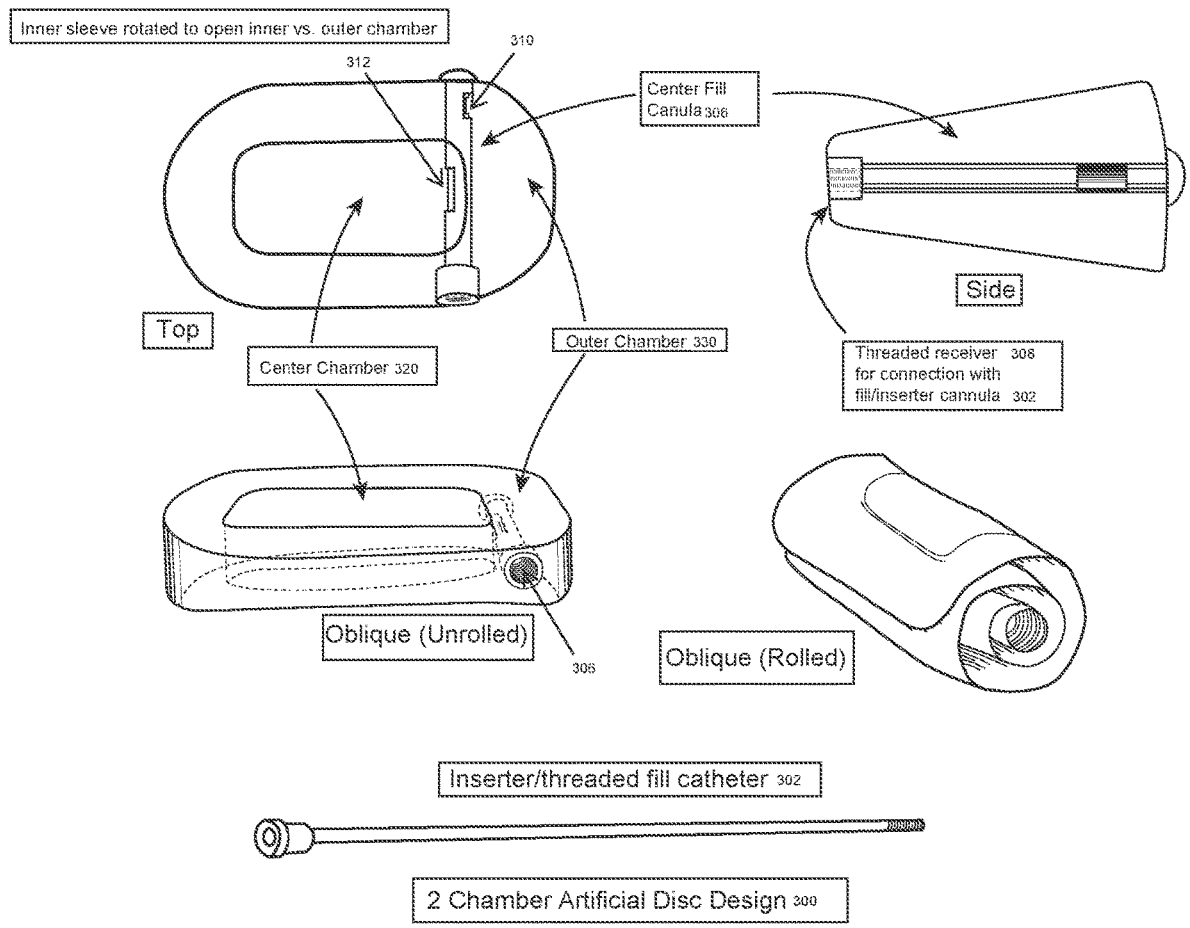
FIG. 21 illustrates a two-chamber artificial disc implant design with separate chamber filling and an inner sleeve for blocking one of the chambers during filling and a rotatable sleeve for closing a current chamber and opening new chamber fill slots.

The implant 200 does not have an attached catheter like the hydrostatic elevator 70 does. This implant 200 has an inner cannula 206 that extends from the posterior aspect of the device to the anterior aspect of the device. This inner cannula 206 can be connected to a fill catheter 202 which is used for both insertion of the device and filling of the device. The implant 200 is rolled around the inner cannula 206 in the same fashion that the hydrostatic elevator 70 is rolled around its inner catheter 71. It is deployed in a fashion similar to the hydrostatic elevator 70 as well as illustrated in FIGS. 18-20. In this embodiment, maintaining the integrity of the graft space cavity is paramount. Therefore nitinol wire could be used to maintain the inner wall of the ellipsoid graft shape. Nitinol may be present on the posterior arm of the graft circumferentially in the instance where lordosis is desired. This allows for expansion of the anterior limb greater than the posterior limb of the ellipsoid implant.

The catheter 202 used to fill and insert the implant 200 can be paired with a 2 to 6 mm diameter graft insertion catheter. The diameter of the catheter implant itself is between 2 and 5 mm. The graft insertion catheter 214 is positioned so that its opening is even with the mouth of the posterior graft window (see FIG. 20). Once the device 200 is inserted into the disc space, the device 200 is filled with cement such as bone cement or methyl methacrylate. This fill goes around the secondary catheter for graft insertion shown in FIG. 20. Once the implant 200 has been filled, the graft insertion tube 214 is used to push graft material such as allograft or autograft into the device's central cavity 216. Once the graft material has been placed, the graft insertion tube 214 is removed and a stylet is run down the cement insertion catheter 202 to push the remaining cement into the device and out of the catheter 202 filling the remaining void left by the removal of the graft insertion tube 214. The cement is allowed to harden prior to removing the cement insertion catheter 202. This completes an anterior lumbar interbody-like construct through a very minimal discectomy exposure as illustrated in FIG. 20.

The implant 200 assumes its predetermined shape when it is filled with the surgeon's choice the materials. These materials could include but are not limited to cement, silicates, liquids such as saline or water, and or a gas such as air. The implant 200, 300 can have one chamber 220 or multiple chambers 320, 330. A central fill tube would be responsible for filling these chambers 320, 330. The central fill tube may have access to all of these chambers. The walls of the implant can be made of silicone, latex, graphene, or polyurethane with implanted material to maintain structural integrity such as nitinol wire or carbon fiber filament.

In one embodiment, the implant container would be ellipsoid in shape, following the vertebral bodies' hypophyseal ring, with a central opening. The hypophyseal ring is the vertebral body's strongest structural element. This is because the vertical walls of the vertebral body and their cortical bone meet the horizontal cortical endplates in a ring that approximates the annular boundary. The central fill tube would pass through the posterior portion of the ellipsoid and run all the way through to the front anterior wall of the ellipsoid. It may or may not pass through the central empty graft cavity. The access channel would allow attachment of a fill catheter that would also be tubular in structure. There would be an opening on the distal and proximal ends of the fill chamber that would allow the fill material to enter and fill the device itself. The device would be placed into the disk space in a rolled state as illustrated in FIG. 19. It would then be unrolled. A secondary graft fill tube would be laid on top of this implant. This secondary fill tube would have its opening emptying into the central graft cavity created by the device as illustrated in FIG. 20. This central cavity is left vacant and the device itself rings around this cavity to allow fusion graft material to be placed in the central portion of the prepared intervertebral space. The interbody container would be filled with original material such as quick setting cement. This would establish a rigid boundary that would completely fill the intra-annular space. This would replicate an anterior interbody fusion graft with an extremely limited annular opening. As the container fills around the secondary graft tube, the graft material is inserted through the secondary tube into the central intervertebral graft cavity. Once the graft material has been completely placed into the cavity, the secondary graft insertion tube can be removed and the filling of the intervertebral container through the primary fill tube can be completed. This seals the annulotomy and sequesters the graft space from the spinal canal. The cement can also fill and seal the device's central fill tube once it solidifies.

In these embodiments all of the benefits of an anterior interbody fusion without the spinal instability issues that arise from a standard anterior interbody exposure are realized. The patient's annulus is effectively used as countertraction against the interbody fusion device. Stability is maintained in all biomechanical spine motions. Use of this fusion method for example would not necessitate additional instrumentation. However, if, for example, a large facetectomy would need to be performed to decompress an exiting nerve root or the patient has a spondylolisthesis that needs to be reduced, the surgeon could opt for additional traditional percutaneous or open spinal instrumentation. The robot can assist with standard instrumentation placement such as pedicle screws, facet screws, or cortical screws.

In another embodiment of the implant 300, two fill chambers 320, 330 are used to replicate the function of a normal intervertebral disc. The materials used to fill these chambers 320, 330 can be selected based on biomechanical data of the normal intervertebral disc space. In one construct, the device 300 could be filled with a more rigid two-phase silicate in the outer-ring 330 in the approximate ellipsoid shape described previously. The central device chamber 320 could then be filled with a fluid such as saline or water. In such a way the normal anatomic stress response of an intervertebral disk space could be replicated without the use of metals. The forces would be distributed equally along the end plates. The novelty of this system is that through further scientific research we can determine the optimum disc replacement material.

The central access port is designed to be backfilled to seal in the container's contents. In fusion example above, the spinal cement would be drawn back through the central portal. This would completely enclose the graph material in a rigid cement ring. In this way the device in the second example could also be self-contained whereby fluid or gas placed into the central chamber 320 could be locked into place by a more rigid fill material used in the outer ring 330.

The center fill cannula 306 comprises two fill ports 310, 312 to allow for filling of the center chamber 320 and outer chamber 330 selectively via rotation of an inner device which opens or closes the fill ports 310, 312 independently. The center fill cannula 306 is configured with a threaded end 308 for threaded connection with a fill cannula 302 and as described above, the fill cannula is configured to allow for selective and independent filling of the central chamber 320 and outer chamber 330.

This system is designed to be path independent. Any surgical approach to the annulus can be accommodated by this system. An appropriate preoperative plan can allow the interbody device and the hydrostatic expansion device to match a given case. A standard discectomy approach allows early adoption of this system because of the approach's ubiquity. Far-lateral posterior approaches, transpsoas approaches, anterior oblique and direct anterior approaches can all be accommodated by this system. The major strength of this system is that it can be utilized through standard approaches already in use by spine surgeons. This approach is buoyed further by allowing selection of an approach that maximizes direct decompression without requiring more incisional invasion. Many minimal access techniques rely on "indirect decompression" meaning the decompression of neurologic elements is assumed rather than directly observed. The ability of this system to maximize decompression and minimize invasiveness is the core concept of the previously described approach.

Control Software

Stereotactic software may account for variance of a stereotactic end effector. All current stereotactic applications use a rigid frame to account for the end position of a similarly rigid, fixed-shape instrument. Because the end effector described herein, the drill shaft and its associated drill bit in these embodiments are variable, the stereotactic software requires a method for monitoring this variance. The stereotactic software may be given the relative position of the articulation control dial's reflective sphere along the sphere's handle housing slide to the reflective spheres attached to the handle housing's fixed stereotactic frame by the stereotactic system's infrared cameras.

Using the handle housing stereotactic frame as a fixed reference, the stereotactic software will account for the changing position of the control dial's reflective stereotactic sphere. In one implementation of this software, a simple trigonometric relationship can be found between any two-handle housing fixed-array reference spheres and the control dial's reflective sphere to form a triangle whose side lengths are known to the software by infrared camera monitoring. Angles of this triangle can be calculated by the software and by calibrating the distance the articulation control dial's reflective sphere moves along its slide for each degree the actual drill extension articulation changes. These changing angles will be represented by the stereotactic software as a virtual change in the drill extension's corresponding articulation (referring back to FIG. 11).

Software may be configured to allow for pre- and intraoperative surgical planning. This is a technique that has been applied to surgeries such as deep brain stimulation in the past. This technique will allow surgeons to evaluate a patient's preoperative or intraoperative imaging and adjust operative strategies. In this embodiment, the disc space to be cleared by the robotically assisted minimally invasive spine system can be defined by the surgeon on pre- or intraoperative imaging. This can be represented by the software visually as a geometric shape such as an elliptic cylinder whose upper and lower boundaries can be assigned by the software as the upper and lower vertebral endplates associated with the given disc space or by user specified custom boundaries. The outer circumference can also be user customized or set so that the volume perimeter does not come within a certain safe distance of the upper and lower endplate boundary, for example a perimeter no closer than 3 mm to the smallest involved endplate boundary can be chosen. This would assume that the volume is completely contained within the patient's radiographically invisible annulus as long as the volume maintains a 3 mm circumferential distance from the inferior and superior vertebral bodies' outer circumference as we know that the annulus attaches circumferentially here. This volume can assist with selection of the spinal implant to be utilized and the appropriate size of any disc space dilation devices to be utilized.

Although the present disclosure has been described with reference to preferred embodiments, workers skilled in the art will recognize that changes may be made in form and detail without departing from the spirit and scope of the disclosure.

The invention claimed is:

1. A method of accounting for and/or monitoring a variance in a position of a stereotactic end effector, the method comprising:
calculating a variation in a first angle between a first movable reference fiducial and two spaced apart stationary reference fiducials based on a distance between the first movable reference fiducial and each of the two stationary reference fiducials wherein the distance between the first movable reference fiducial and each of the two stationary fiducials is determined by a camera;
calculating a variation in a second angle between a second movable reference fiducial and the two spaced apart stationary reference fiducials based on a distance between the second movable reference fiducial and each of the two stationary reference fiducials wherein the distance between the second movable reference fiducial and each of the two stationary fiducials is determined by the camera; and
correlating a calculated variation in the first and second angles to variations in a position of an end effector to determine a location, position, orientation, or combination thereof of the end effector.

2. The method of claim 1, wherein a plurality of stationary reference fiducials are provided on a stereotactic frame and using any two of the plurality of stationary reference fiducials for calculating the variation in the angle between the first movable reference fiducial and the two stationary reference fiducials.

3. The method of claim 2 wherein the stereotactic frame is a Y shaped frame supporting three stationary reference fiducials.

4. The method of claim 2 wherein the stereotactic frame is rigidly secured to a housing for steering components of the end effector.

5. The method of claim 4, wherein the movable reference fiducials comprise reflective spheres, each reflective sphere coupled to a control dial on the housing and wherein rotating one or each dials concurrently changes at least one of a position, orientation, articulation, location or combination thereof of the end effector.

6. The method of claim 4, wherein the movable reference fiducials comprise reflective spheres, each reflective sphere coupled to a control dial on the housing, and wherein rotating each dial linearly moves the corresponding reflective sphere along an opening in the housing.

7. The method of claim 1 wherein the stationary reference fiducials and movable reference fiducials each comprise reflective stereotactic spheres.

8. The method of claim 1 and using one or more cameras comprising an infrared camera to determine a distance between the first or second movable fiducials and the two spaced apart stationary reference fiducials forming a triangle and monitoring variance in an angle at the movable reference fiducial with respect to the two spaced apart stationary reference fiducials.

9. The method of claim 1 wherein the end effector is an articulating drill extension.

10. A method of accounting for and/or monitoring a variance of a stereotactic end effector, the method comprising:
correlating a rotational movement of a control dial for the end effector to a linear movement of a reflective stereotactic sphere coupled to the control dial;
using a stereotactic frame coupled to a housing also supporting the control dial as a fixed reference point;
accounting for a changing position of the reflective stereotactic sphere with respect to one or more points on the stereotactic frame by determining a distance between the reflective stereotactic sphere and each of the one or more points on the stereotactic frame with an infrared camera;
using a trigonometric relationship between any two points on the stereotactic frame and the reflective stereotactic sphere to calculate one or more angles of a triangle formed between the two points and the reflective stereotactic sphere; and
representing changing angles as a virtual change in an articulation of the stereotactic end effector.

11. The method of claim 10 wherein the stereotactic frame comprises an array of reflective stereotactic spheres.

12. The method of claim 11 wherein the stereotactic frame is rigidly coupled to a robotic arm and the end effector is an articulating drill extension and the method allows for robotically assisted minimally invasive spinal surgery.

13. The method of claim 10 and further comprising representing or displaying visually, as a geometric shape, boundaries corresponding to upper and lower vertebral endplates associated with a given disc space or by user specified custom boundaries.

* * * * *